United States Patent
Apple et al.

(10) Patent No.: US 6,251,059 B1
(45) Date of Patent: *Jun. 26, 2001

(54) MEDICAL RADIATION TREATMENT DELIVERY APPARATUS

(75) Inventors: Marc G. Apple, Fort Wayne; Brian L. Bates; John A. DeFord, both of Bloomington; Neal E. Fearnot, West Lafayette, all of IN (US)

(73) Assignees: Cook Incorporated, Bloomington; MED Institute, Inc., West Lafayette, both of IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/262,620

(22) Filed: Mar. 4, 1999

Related U.S. Application Data

(63) Continuation-in-part of application No. 09/150,814, filed on Sep. 11, 1998, now Pat. No. 6,159,141.
(60) Provisional application No. 60/077,046, filed on Mar. 6, 1998, and provisional application No. 60/058,547, filed on Sep. 11, 1997.

(51) Int. Cl.[7] .................................................... A61N 5/00
(52) U.S. Cl. .................................................. 600/3
(58) Field of Search ............................................ 600/1–8

(56) References Cited

U.S. PATENT DOCUMENTS

| | | |
|---|---|---|
| 4,029,104 | 6/1977 | Kerber . |
| 4,192,438 | 3/1980 | Foster et al. . |
| 4,208,588 | 6/1980 | Rudin . |
| 4,254,774 | 3/1981 | Boretos . |
| 4,328,811 | 5/1982 | Fogarty . |
| 4,565,301 | 1/1986 | Hubbard et al. . |
| 4,815,449 | 3/1989 | Horowitz . |
| 4,823,167 | 4/1989 | Manska et al. . |
| 5,087,247 | 2/1992 | Horn et al. . |
| 5,112,305 | 5/1992 | Barath et al. . |
| 5,227,969 | 7/1993 | Waggener et al. . |
| 5,423,744 | 6/1995 | Gencheff et al. . |
| 5,427,104 | 6/1995 | Briend et al. . |
| 5,429,582 | 7/1995 | Williams . |
| 5,458,571 | 10/1995 | Lampropoulos et al. . |
| 5,464,395 | 11/1995 | Faxon et al. . |
| 5,484,384 | 1/1996 | Fearnot . |

(List continued on next page.)

OTHER PUBLICATIONS

Intra–Arterial [90]Y Brachytherapy: Preliminary Dosimeteric Study Using a Specially Modified Angioplasty Balloon; Int. J. Radiation Oncology Biol. Phys.; vol. 33, No. 3; pp. 713–717; 1995.

*Primary Examiner*—John P. Lacyk
(74) *Attorney, Agent, or Firm*—Anton P. Ness; Richard J. Godlewski

(57) ABSTRACT

A catheter apparatus (20) and radiation dosimetry unit indicator (21) for delivery of a prescribed radiation dose to a patient. The catheter is filled with a radiation carrier material such as an inert radioactive gas (12) for the treatment of, for example, restenosis after angioplasty, and malignancies. The inflated catheter includes a plurality of discrete chambers such as balloon sections (22, 24, 26) for transporting the radioactive carrier material, and a plurality of discrete chambers (32, 34, 36) enabling substantial blood flow through the artery during treatment with the prescribed radiation. The inflated catheter can also comprise a one-unit balloon. A specific metal coating enhances the radiation dose delivered to the target. The wall (25) of the inflation lumen attenuates transmission dose to the blood circulating through the hollow inner lumen of the catheter device. The system also creates increased by-product radiation, from the impact of beta particles and gamma protons traveling toward the lumen wall. A radiation dosimetry unit indicator (21) is positioned, disposed, or affixed to a calibrated catheter to assist the physician in prescribing radiation activity and exposure times.

10 Claims, 14 Drawing Sheets

U.S. PATENT DOCUMENTS

| | | |
|---|---|---|
| 5,485,835 | 1/1996 | Vande Streek et al. . |
| 5,503,613 | 4/1996 | Weinberger . |
| 5,528,652 | 6/1996 | Smith et al. . |
| 5,536,341 | 7/1996 | Kelman . |
| 5,540,659 | 7/1996 | Teirstein . |
| 5,556,389 | 9/1996 | Liprie . |
| 5,571,086 | 11/1996 | Kaplan et al. . |
| 5,616,114 | 4/1997 | Thornton et al. . |
| 5,618,266 | 4/1997 | Liprie . |
| 5,916,143 | 6/1999 | Apple et al. . |

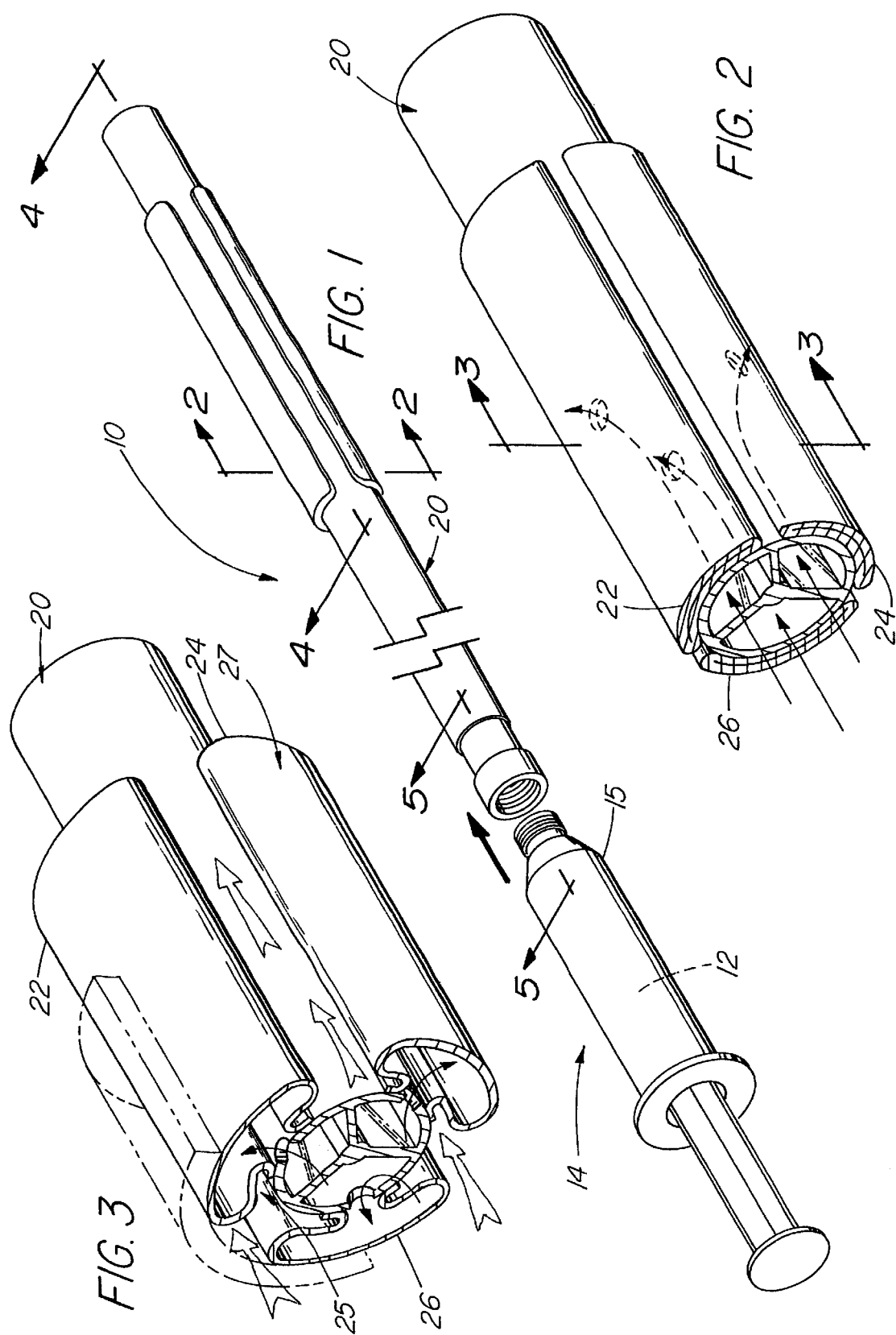

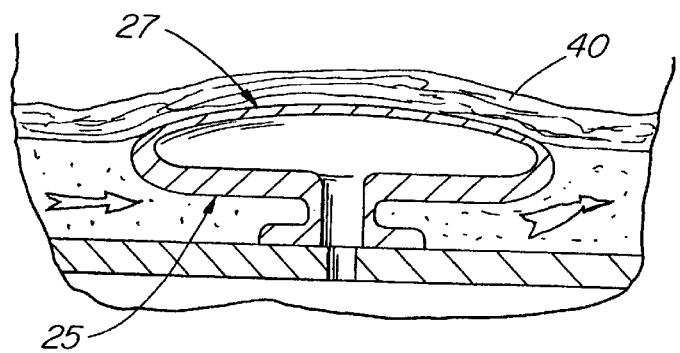
FIG. 7
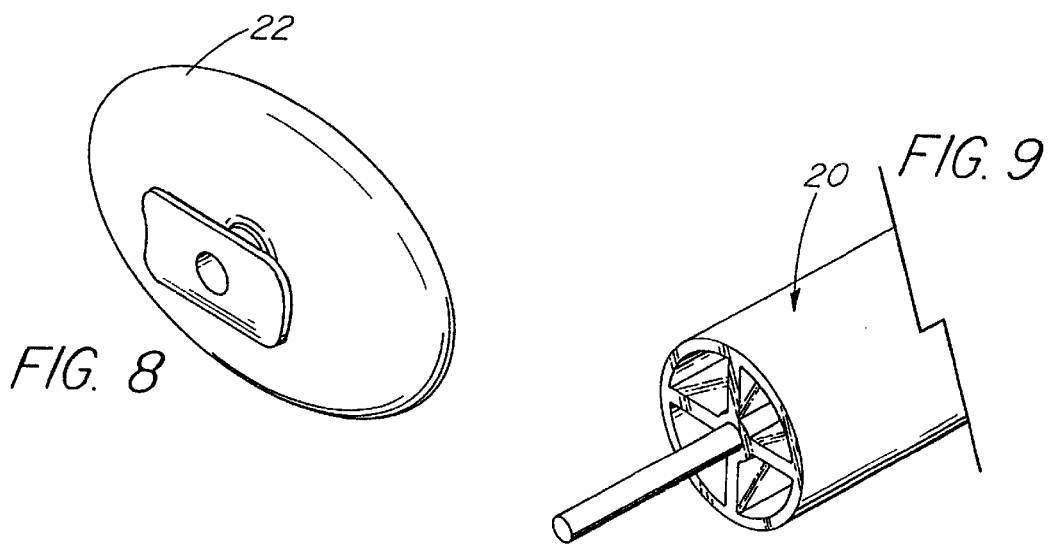
FIG. 8
FIG. 9
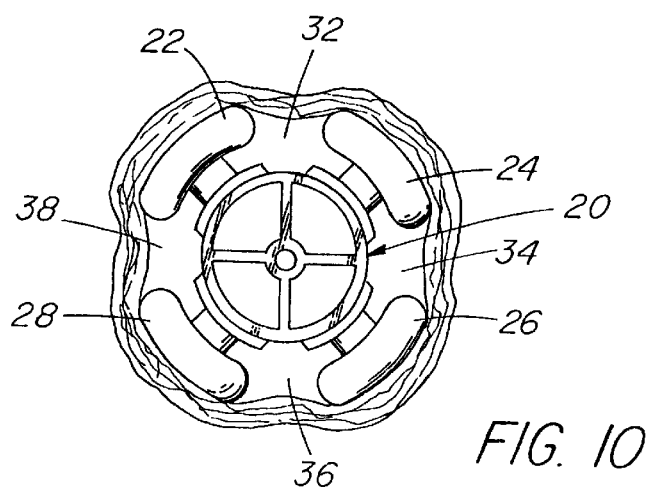
FIG. 10

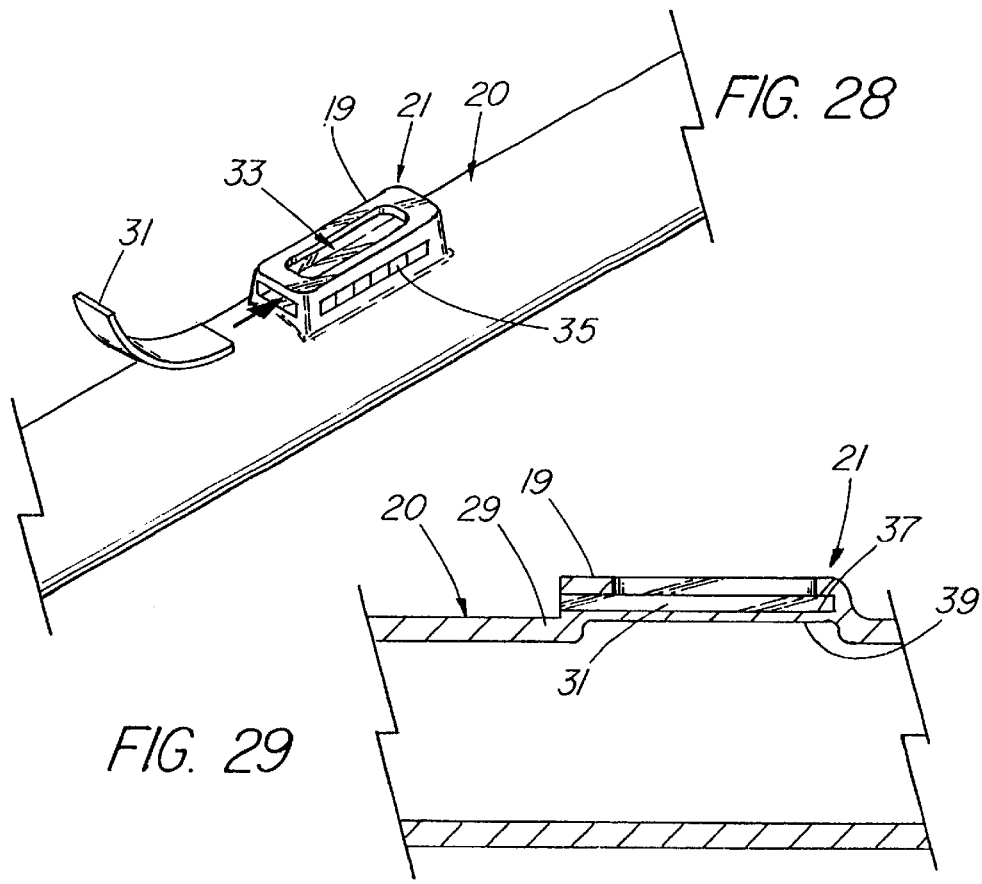
FIG. 28
FIG. 29
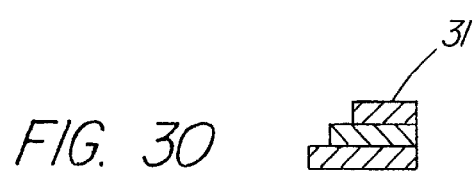
FIG. 30
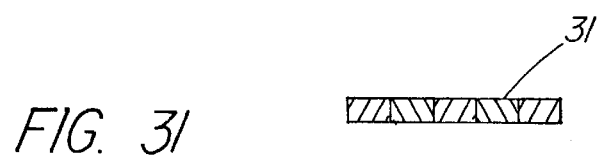
FIG. 31

MEDICAL RADIATION TREATMENT DELIVERY APPARATUS

CROSS-REFERENCE TO RELATED APPLICATIONS

This application claims priority of provisional application Ser. No. 60/077,046, filed Mar. 6, 1998, and is a continuation-in-part of U.S. patent application Ser. No. 09/150,814, filed Sep. 11, 1998, now U.S. Pat. No. 6,159,141; which claims priority to provisional application Ser. No. 60/058,547, filed Sep. 11, 1997.

TECHNICAL FIELD

This invention relates generally to medical devices and, in particular, to medical radiation treatment delivery apparatus such as a catheter for administering a radiation treatment to a patient.

BACKGROUND OF THE INVENTION

Angioplasty is an established procedure for reducing the effect of atherosclerotic plaque on and intraluminal narrowing of the arterial walls within the vascular system of the patient. The effect is reduced by use of a catheter that is inserted into the site of the diseased-occluded vessel. A balloon portion of the catheter is then inflated to a predetermined pressure range and size, to radially compress the plaque occlusion, thereby increasing the internal diameter of the previously restricted artery. The balloon is then collapsed and the catheter is removed.

After the angioplasty procedure has been performed, as many as one-third to one-half of the patients soon develop restenosis. Restenosis can occur after angioplasty or other recannulation procedures, with or without stenting, wherein the migration and proliferation of benign cells cause a restenotic lesion to form, resulting in the further blockage of the intravascular structure.

Radiation is administered to patients for a variety of reasons, such as to treat restenosis, malignant or benign tumors, or the like. Examples of such treatments are disclosed in U.S. Pat. Nos. 5,059,166; 5,213,561; and 5,302,168.

It would be preferred to be able to provide a radiation delivery system which would:

a) deliver a predetermined totally-cumulative and homogeneous dose of radiation to the lesion site, at a predetermined penetration depth, while minimizing the exposure of surrounding healthy tissue to the radiation;

b) enable the treating physician or other health-care personnel to be bedside to the patient during the administration of the radiation therapy without exposing the physician or health care personnel to any unreasonable risk;

c) use radiation material that is readily and inexpensively available from a commercial provider;

d) use minimal special equipment storage, or delivery devices, except for routine facilities available in most nuclear medicine or radiation oncology departments;

e) use a radiation carrier material that if applied as an unsealed free-gas form, the inert, noble gas properties essentially enable the molecules of the carrier material to rapidly dissipate throughout the body of the patient without any prolonged organ accumulation or chemical interaction, and rapid dilution of the carrier material is quickly re-released from the bloodstream through the lungs;

f) minimize long term occlusion of normal blood flow during therapy, thereby providing more flexibility as to administration time and dosage;

g) use a radiation carrier material that is stable and which can be pressurized, stored, and made to high millicurie activity per cubic centimeter with reasonable cost and availability;

h) use beta particles having excellent initial dose rate delivery and energy transfer when directly adjacent to the targeted tissue within the first one millimeter, and not penetrate much beyond this depth;

i) use gamma photon energies having depth doses that provide complementary dose deposition with the beta particles for the first one millimeter, and primary additive dose delivery for an additional two to three millimeters of the targeted tissue;

j) use these beneficial physical and biological radiation properties for treating restenosis, and malignancies (for example—in the brain, lung, esophagus, trachea, cervix, biliary ductal system, colon or rectum, the gastrointestinal system, the gynecological system, or head and neck) and other internal ailments where an internal application of radiation directly applied to the tissue may be needed; and k) attenuate the transmission dose to blood circulating through the apparatus, and while creating increased by-product radiation, delivering useful radiation dose over hundreds of micrometers of target tissue.

SUMMARY OF THE INVENTION

The foregoing problems are solved and a technical advance is achieved in illustrative medical radiation treatment delivery apparatus such as an inflatable balloon catheter for delivering radiation to a treatment site. In particular, the apparatus has a portion such as the inflatable balloon through which radiation from a radioactive fluid such as an isotope of xenon can be radiated. The balloon normally has a radiation dosimetry unit of measurement such as a radiation dose rate which heretofore had to be calibrated by a medical physicist or medical radiation expert for providing a prescribed radiation dose within prescribed limits to the patient. This radiation dosimetry unit of measurement is advantageously indicated by the manufacturer and affixed, disposed or positioned on the delivery device as an indicator of the radiation dosimetry unit of measurement.

In one embodiment, the dosimetry unit is simply displayed on or near an end of the catheter apparatus with one or more symbols, letters, or numbers indicative of the dosimetry unit. The indicator can be affixed, disposed, or positioned thereon by printing, photoetching, painting, embossing, raising, or any other method of marking.

In another aspect, the indicator can be a radiation sensitive film which is sensitive to radiation for changing from one visible shade to another. This advantageously can be used to supply information to the attending physician for the purposes of radiation treatment and, in particular, achieved total delivered dose in vivo. Furthermore, this radiation sensitive film can be used either alone or in combination with one or more other dosimetry use indicators to provide the attending physician with a host of information concerning the properties of the catheter or delivery apparatus or the use thereof in patients.

The elongated member of the catheter apparatus comprises at least one of a polyurethane, polyethylene, polyimide, polyvinyl chloride, polyamide, polytetrafluoroethylene, silicone material, or any other similar suitable material. A high density material of at least one of barium, tungsten, lead, tantalum, titanium, bismuth, gold, platinum, palladium, rhodium, or any other similar suitable material is also included in the elongated member to advantageously control the dosimetry unit of the catheter as well as provide radiation shielding for the patient and attending personnel. Similarly, the material of the portion of the delivery apparatus that comes in contact with the treated tissue such as the inflatable balloon(s) advantageously includes at least one of silicone, latex, a synthetic material similar to latex, polyamide, vinyl, polyethylene, polytetrafluoroethylene, polyethylene terephthalate, fluorinated ethylene propylene, or any other similar suitable material. Selection of the balloon material and its density and thickness affect the radiation dosimetry unit of measurement such as the radiation dosage rate. High density materials as previously mentioned, also are advantageously utilized to control the dosimetry unit.

The system of the present invention is useful for the administration of ionizing or other types of therapeutic radiation. The intravascular catheter system of the present invention uses either of several unique radiation carrier fluids. The catheter apparatus includes either a plurality of balloon sections or a single balloon unit which is inflatable by an inert radioactive carrier fluid (liquid or gas). In one aspect, blood or other body fluid flows through the artery or tube and possibly the catheter when the balloon sections are deflated and inflated. When the balloon(s) of the several embodiments is inflated, the blood flows through at least one section(s) disposed between and/or within the balloon section(s). The system can also be readily modified for tissue or organ-specific design to treat malignancies in passageways or tubes of cancer patients, or even injecting the radio-contents of the catheter into tissue in a limited, controlled manner.

In one embodiment of the present invention, one catheter can perform the two functions of angioplasty as well as the treatment of restenosis, although specific expansion pressures would need to accurately accommodate allowances for tissue dosimetry with respect to balloon thickness, density, materials, etc. The radioactive fluid can initially be used to expand the balloon section, to perform the angioplasty, and then left in situ to prevent or minimize restenosis. Alternatively, the initial expansion for the angioplasty can be performed by introduction of a discrete fluid such as a liquid, which can be removed and replaced by the radioactive fluid such as a radioactive gas. Multiple separate lesions can be treated with the same catheter. As another alternative, the same balloon with radiofluid/xenon gas can be used for synchronous brachytherapy with stent placement.

As a further alternative, the angioplasty catheter can, after it has fulfilled its normal function, be withdrawn and replaced by the catheter apparatus described herein. A lesser number of changes of the catheter is better for the patient, since any intrusion into the body, especially the coronary arteries, can be damaging.

The catheter is designed to be capable of direct insertion into any tumor as well as pseudocavities or defects after surgical or other debulking/resection procedures, or to be maneuverable into a position adjacent to a tumor such as by being maneuverable into a body cavity or along a body passageway through which body fluids will pass. When the catheter is used in a vein or artery, the device can be made to permit the flow of blood within the catheter such as between and/or inside the balloon or balloons or to maintain perfusion flow via the central lumen. Provision is also made for variable balloon(s) thicknesses to provide radiation shielding for the blood and/or redirecting the radiation to the treatment tissue.

Shielding can also be accomplished or effected by an outer shield surrounding the balloon(s). The outer shield can be pulled back proximally to allow the balloon(s) to inflate fully or partially. The proximal end of the outer shield in combination with markings on the proximal end of the catheter are accomplished or effected as a dosimetry unit indicator. This is accomplished by varying the volume of the inflatable balloon(s). As the outer shield is pulled back, the length of the balloon(s) that is allowed to inflate increases, thereby increasing the volume of the balloon(s). This, in turn, affects the total radiation dose, radiation dosage rate of the balloon(s), etc. The change in length is calibrated and indicated by the combination of the markings on the proximal end of the catheter and the proximal end out of the outer shield. In addition to being a dosimetry unit(s) indicator, the outer shield also advantageously provides radiation protection to non-treatment site tissue of the patient and to attending personnel.

The balloon section can either comprise a single balloon or a plurality of balloons arranged on the catheter section either peripherally or longitudinally or both. The section is inflated by the radiation fluid that causes the exterior parts of the balloon(s) to improve contact with the tissue to be treated. There can be an exterior inflatable coating of the catheter movable into contact with the tissue. The contact can also be direct between the balloon(s) and the tissue to be treated. The wall of the balloon(s) in the region of the tissue to be treated is of reduced thickness in order to maximize the radiation to the tissue. The thickness obviously must be sufficient to prevent leakage of radiation fluid. The higher the activity, the more important the question of leakage becomes. The balloon when inflated with a radioactive gas such as xenon can also conform to the tissue to be treated to provide homogeneous radiation delivery.

The treatment method of the present invention can be applied to a patient either after angioplasty has been performed, or for treating malignant tissue within the brain, lung, esophagus, trachea, cervix, biliary ductal system, colon or rectum, the gastrointestinal system, the gynecological system, on the skin, on ocular structures, head and neck, or other areas accessible to this catheter technology.

The method is designed to apply ionizing radiation prophylactically to post-angioplasty vascular tissue or tumors internal to a patient while minimizing exposure of healthy tissue. Initially, the location and the size of the tissue to be treated are clinically identified, perhaps, with a fluoroscope. The catheter apparatus is then introduced and positioned adjacent to or within the tissue to be treated. The catheter apparatus is then inflated by the radioactive fluid (e.g., gas) thereby exposing the tissue to be treated to radiation. The catheter can include a plurality of discrete balloon sections with special and hypo-dense material, which enable the inflated catheter to match and/or conform more closely with the internal tissue wall, and minimize the amount of gas loss internal to the patient in the event of leakage. In one embodiment of the invention, the inflation lumen of the delivery catheter is minimized to decrease the amount of radioactive fluid in the delivery catheter, as well as the amount required in the injection source. The catheter apparatus can include an outer retractable radiation sleeve or shield to prevent the exposure of healthy tissue to radiation. In addition, the radiation shield can be used to control the delivery of radiation to the tissue to be treated. The radiation shield is then retracted to a specific measurable length.

Preferably, the radioactive fluid is an inert gas, such as xenon or an isotope of xenon, and emits beta and gamma particles into the tissue to be treated. The catheter apparatus can also include a outer layer containing a shielding material that is deposited upon the outer surface of the catheter by one of several well-known methods. Alternatively, the shielding layer can be comprised of a film that is bonded to or shrunk over the outer surface of the delivery catheter.

A specific coating of integrated and/or layered transitional metal or metal alloy compounds from the surface to the center of the gas-exposed side of the wall of the central catheter lumen enhances the radiation dose delivered to the targeted tissue. The wall of the lumen attenuates transmission dose to the blood circulating through the hollow inner lumen of the catheter device. Also, the system creates increased by-product radiation, from the impact of beta particles and gamma photons traveling toward the lumen wall. This energy would otherwise be wasted as treatment dose, but instead produces by-product low-energy x-ray photons which increase the deposited energy dose into the target tissue via scattered angle coincidence or secondary redirected x-ray production from the slowing of beta particles traveling into the metal compound on the wall surface. The by-product x-rays travel through the balloon outer wall and deliver useful radiation dose to the targeted tissue (bremsstrahlung).

Another embodiment includes first and second opposing and separate, semi-circular balloons with opposed support displacers attached just proximal and distal to the balloon lengths, upon the outer lumen wall. The built-in injection port unit enables gas-tight redirection of radioactive gas flow from one balloon to the other, one balloon being inflated and delivering treatment dose, while the opposing balloon is deflated. The support displacers are juxtaposed against the vessel wall enabling blood to flow more easily through the space opposite to the treatment side.

BRIEF DESCRIPTION OF THE DRAWING

As the invention can be embodied in many forms without departing from the spirit of essential characteristics thereof, it is expressly understood that the drawings are for purposes of illustration and description only, and are not intended as a definition of the limits of the invention. Throughout the description, like reference numbers refer to the same component throughout the several views.

FIG. 1 is an assembly drawing of one embodiment of the catheter system of the present invention;

FIG. 2 is a detail sectional view of the deflated catheter apparatus taken along line 2—2 of FIG. 1;

FIG. 3 is a detail sectional view of the fully-inflated catheter apparatus taken along line 3—3 of FIG. 2;

FIG. 7 is an isometric view of a second embodiment disclosing a detail sectional view of a balloon of a catheter apparatus being fully-inflated and having a thickened interior wall and a thinner, hypo-dense outer wall;

FIG. 8 discloses a detail of an inflated balloon of the catheter apparatus shown in FIG. 7;

FIG. 9 discloses a third embodiment of the catheter apparatus having a removable central lumen guide/localizing wire that is radio-opaque;

FIG. 10 is a detail sectional view of the fully-inflated catheter apparatus of FIG. 9 within the arterial wall;

FIG. 28 is an enlarged, pictorial, proximal end view of the catheter apparatus of FIG. 1 with an alternative embodiment of an indicator thereon;

FIG. 29 is an enlarged, longitudinally sectioned view of the elongated member of the catheter apparatus of FIG. 1 taken along a line through the dosimetry indicator thereof;

FIG. 30 is an enlarged sectional view of an alternative embodiment of the radiation sensitive film of FIG. 28;

FIG. 31 is an isometric view of an enlarged sectional view of another alternative embodiment of the radiation sensitive film of FIG. 28;

DETAILED DESCRIPTION

Figure 4:
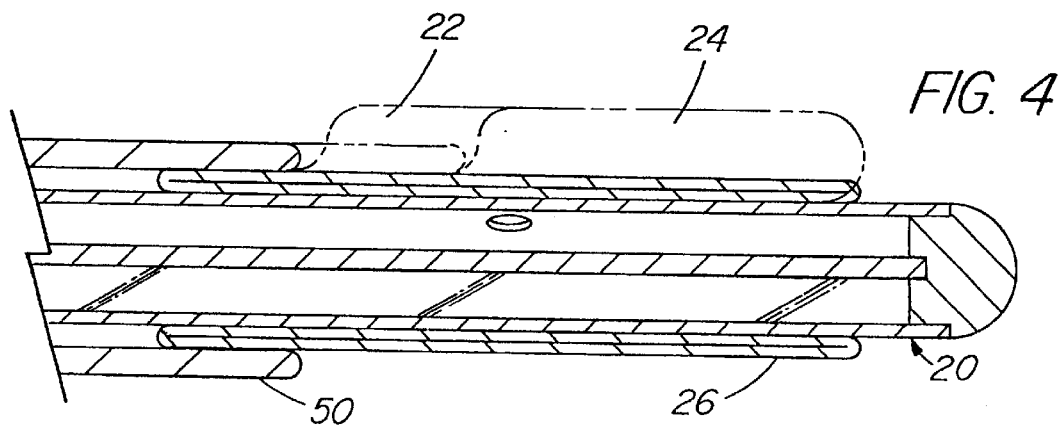
FIG. 4 is a detail sectional view of the deflated catheter apparatus taken along line 4—4 of FIG. 1.
Figure 5:
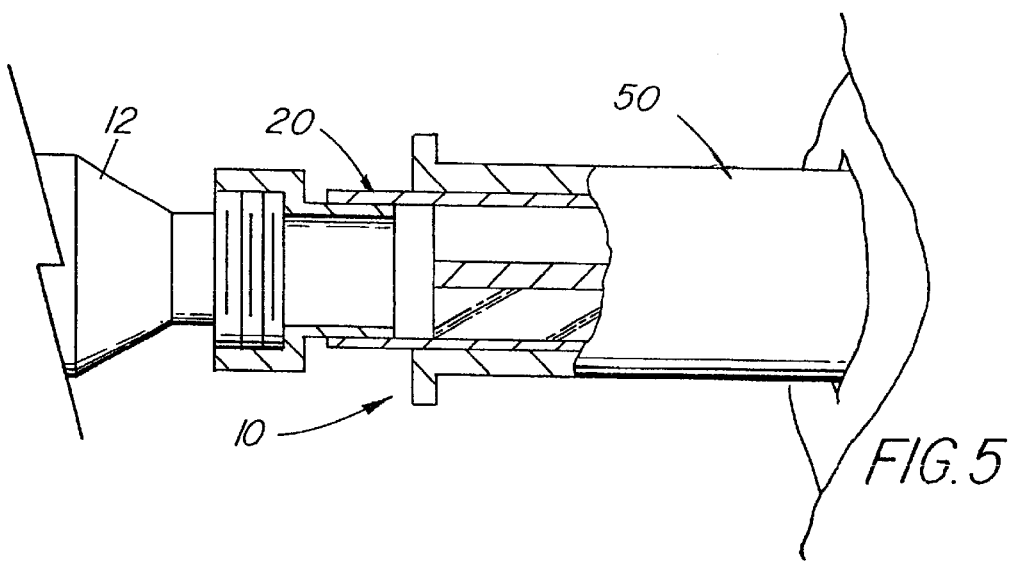
FIG. 5 is an enlarged sectional view of the engagement between the protected, syringed gas supply and the catheter apparatus of FIG. 1.
Figure 6:
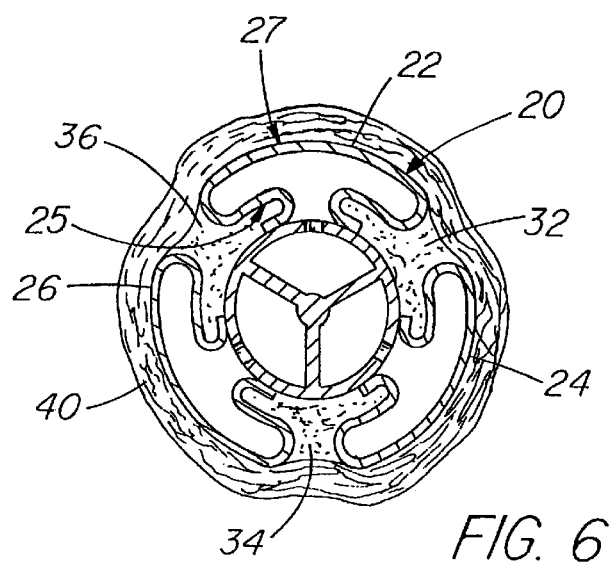
FIG. 6 is a detail sectional view of the fully-inflated catheter apparatus as shown in FIG. 1 inside an arterial wall.
Figure 11:
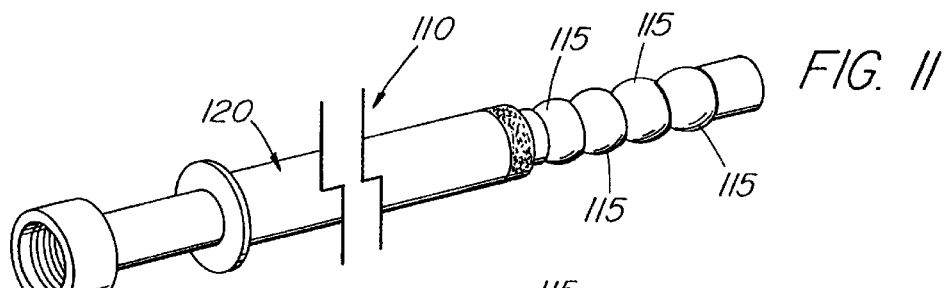
FIG. 11 is an assembly drawing of a fourth embodiment of the catheter system of the present invention with the catheter apparatus being deflated.
Figure 12:
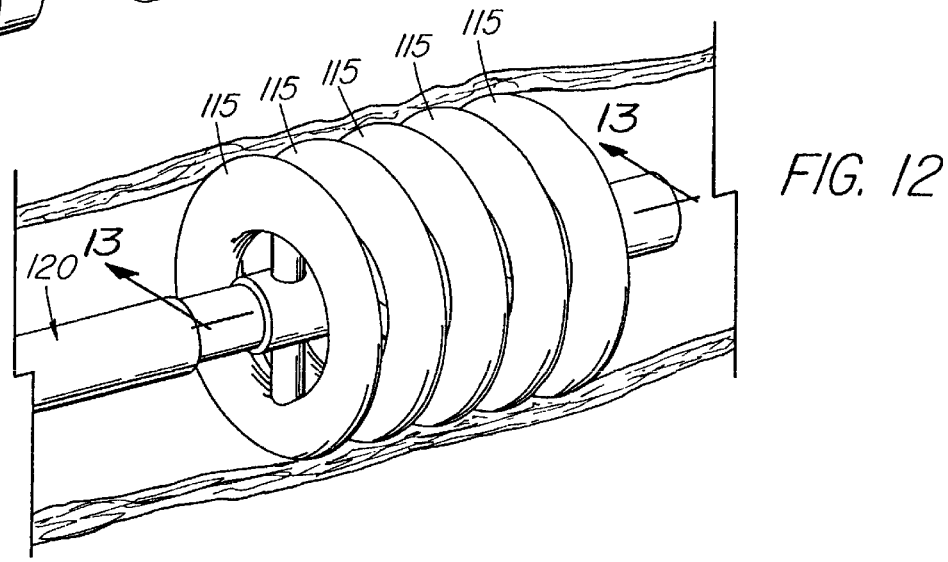
FIG. 12 discloses a detail view of the fully-inflated catheter apparatus of FIG. 11.
Figure 13:
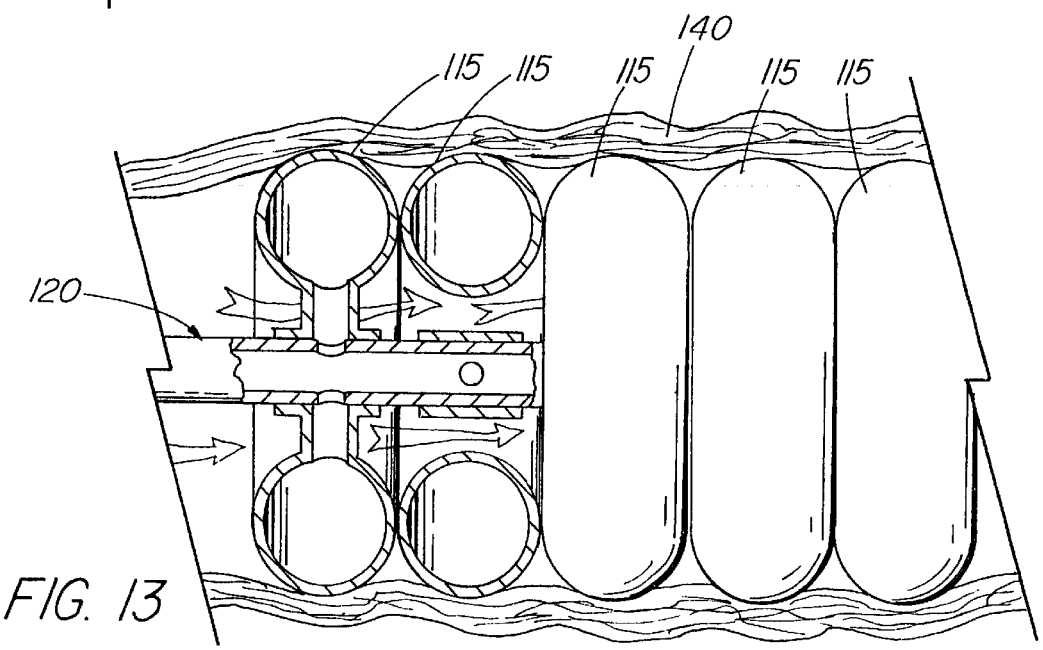
FIG. 13 is a detail sectional view of the fully-inflated catheter apparatus taken along line 12—12 of FIG. 12.
Figure 14:
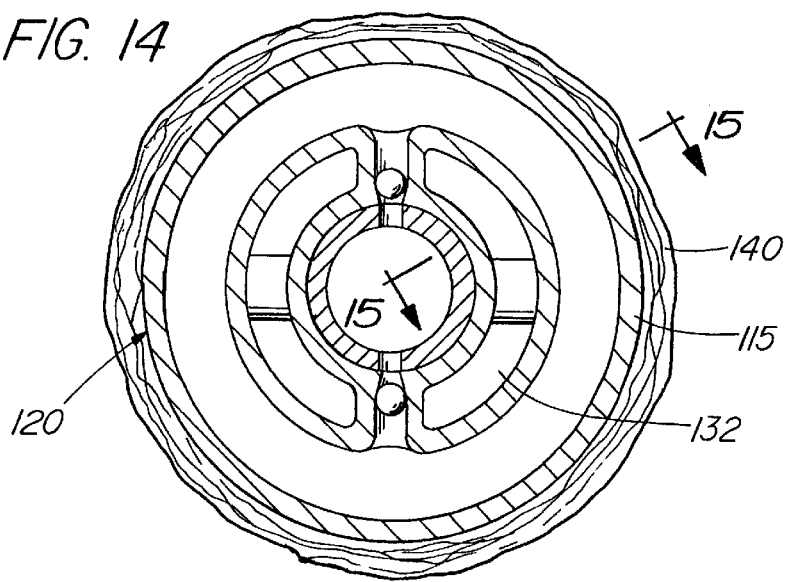
FIG. 14 is a detailed sectional view of the fully-inflated catheter apparatus of FIG. 11.
Figure 15:
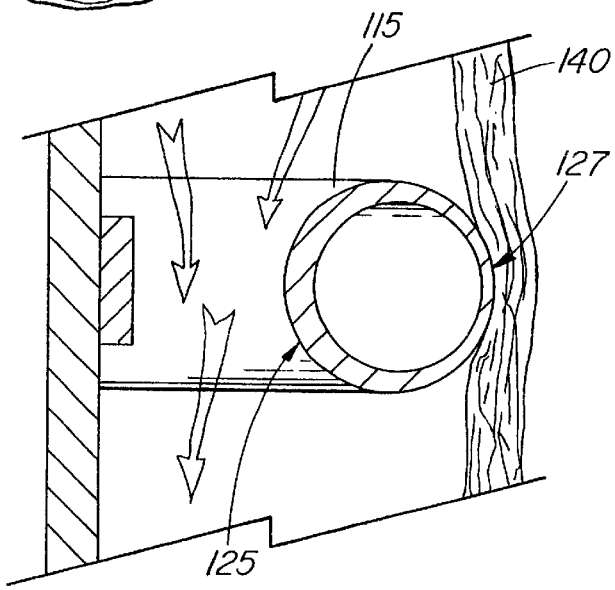
FIG. 15 is an exploded sectional view of a fully-inflated balloon of the catheter apparatus of FIG. 14, the balloon having a thickened inner wall and a thinner hypo-dense outer wall.

FIGS. 1 to 6 disclose one embodiment of medical radiation treatment delivery apparatus 10 of the present invention which includes a supply of radioactive fluid, preferably gas 12, and a radioactive fluid delivery system such as balloon catheter apparatus 20. Preferably, the balloon catheter apparatus 20 is made of latex or a similar synthetic compound, commonly used for intravascular applications, and void of any silicon-based or other metal-based materials. The balloon catheter apparatus is disposable after each patient use, and is designed to handle peak expected pressures less than those used in conventional angioplasty. These pressures typically range from one to ten atmospheres.

As used herein, the term "fluid" includes any gas, liquid, or gel-type substance that generally conforms to the shape of the container within which it is held, and is fluent. While the catheter apparatus of the present invention is used in conjunction with a radioactive carrier fluid, it is preferred that the fluid is a gas, and for reasons hereinafter set forth, an inert gas, such as preferably xenon, or an isotope of xenon. A radioactive gas such as xenon in combination the at least one balloon section preferably provides a homogeneous radiation delivery to the tissue to be treated. The lower pressure gas allows the balloon section to conform to or match with the tissue to be treated. However, the present invention is not limited to xenon gas or an isotope thereof, and the preferred fluid includes all gases and isotopes thereof, radioactive gases or radiogases (inert and/or non-inert) or gases capable of fluorescence, phosphorescence, or luminescence (electron stimulation). Examples of gases include, but are not limited to, xenon, krypton, neon, radon and their isotopes. A radiogas can be dissolved in a liquid or solution (sterile) and be used as a liquid radiofluid. Liquids include all isotopes of liquids and solutions. An isotope can be radioactive or non-radioactive. Radioactive includes nuclear (nucleus) decay of an atom. A radionuclide is any radioactive atom. Fluorescence, phosphorescence or luminescence is associated with electron instability and subsequent emission of radiant energy. Liquids also include all gases dissolved in liquids or solutions. Examples of liquids include, but are not limited to, liquid phosphorus, rhenium, yttrium, technetium, iodine, gallium, chromium, strontium, thallium, samarium, ytterbium, palladium, and all isotopes thereof, and all compounding and binding solutions thereof. All gels utilizing the aforementioned gases or liquids (solutions) are also contemplated. Additional radionuclides can include osmium, vanadium, ruthenium, bismuth, or other transitional heavy metals and their isotopes for liquid and/or gel-type compounding. All inert dual photon/electron emitting radionuclides are further contemplated as well as all inert single particle radio-emitting nuclides and all non-inert radionuclides thereof. Still further contemplated are all inert or non-inert radiofluids which use electron stimulation to produce by-product fluorescent, phosphorescent or luminescent radiant energy for patient treatment. The use of by-product radiant energy emissions including fluorescent, phosphorescent or luminescent emissions can be utilized for therapeutic treatment. Implementation of radionuclide and by-product radiant energy emissions can be applied by the use of the catheter apparatus in the following combinations;

(a) gases and/or fluids or single fluids alone either as a gas—gas or gas-liquid, and/or either inert or non-inert, and/or radioactive or non-radioactive such that the photon or electron emissions of one radiofluid can induce electron shift, scatter, or a quantum level change in the electron shell of the same or other combined "fluid" atoms thereby causing production of relatively low energy photon/electron (possibly in a cascaded amplification) emissions into the targeted tissue as a controlled/calculated dose;

(b) radiofluid(s) as described in (a), except that induction of listed radiant energy is provided via electrical source stimulation from an electrode, cathode, wire or other transmission source such that controlled electrical currents and/or electrical potential delivered through the catheter to the radiofluid or non-radiofluid of the balloon catheter which causes expected electron excitation and/or quantum level fluctuations with by-product fluorescence, phosphorescence and/or luminescence for the aforementioned therapeutic treatments; and (c) phosphorus and/or other known fluorescent metals or alloys are implanted in the balloon material and/or catheter structure so that the combinations described in (a) and (b); radioemission, by-product decay energy and/or direct electrical stimulation, can cause effect on the implanted/layered materials so as to create fluorescent, phosphorescent or luminescent energy delivery as these materials stabilize their electron structure after such stimulation.

The unique medical radiation treatment delivery apparatus 10 of the present invention uses a radioactive fluid. The catheter apparatus 20 includes a single balloon or a plurality of balloon sections 22, 24, and 26, which are inflated with the radioactive fluid. Residual blood flows through the vessel when the balloon or balloon sections 22, 24, and 26 are inflated through a plurality of interposed sections 32, 34, and 36 disposed between the balloon sections.

Figure 25:
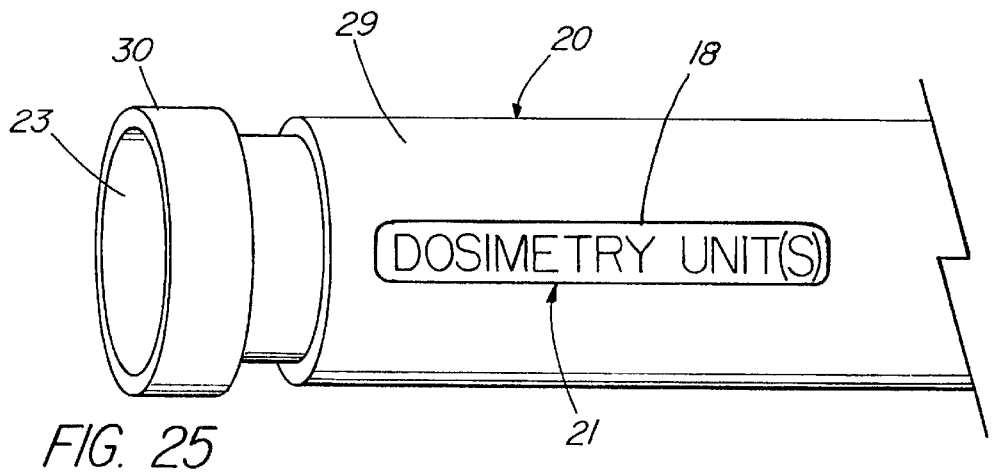
FIG. 25 is an enlarged, pictorial, proximal end view of the catheter apparatus of FIG. 1 with a radiation dosimetry unit(s) indicated thereon.

FIG. 25 depicts an enlarged, pictorial, proximal end view of a medical fluid delivery system such as catheter apparatus 20 of FIG. 1. Affixed, positioned, disposed, or connected to, on, or about the outer surface of catheter apparatus 20 near the distal end thereof is indicator 21, which is indicative of a radiation dosimetry unit of measurement 18. By way of example, radiation dosimetry unit of measurement 18 is at least indicative of the radiation that can be radiated through at least one portion of the catheter apparatus. The at least one portion of the catheter apparatus includes preferably a single balloon or balloon sections 22, 24, and 26, which are inflated with a radioactive fluid. The radiation dosimetry unit of measurement for the balloon or balloon sections of the catheter apparatus can include, but is not limited to, radiation dose rate, total radiation dose at a predetermined tissue depth, radiation source activity, radiation time exposure, tissue depth of a radiation dose, radiation source, or an incidental radiation dose rate. The total radiation dose at a reference tissue depth for a radioactive fluid delivery device such as catheter apparatus 20 is approximately equal to the radiation source activity (i.e., specific activity in millicuries per volume or density unit) multiplied by the radiation dose rate of the device multiplied by the exposure time of the radioactive fluid source. By way of example, a typical prescribed total radiation dose for a radiation delivery device such as catheter apparatus 20 can be 1400 CentiGay. This total radiation dose rate is referenced to a tissue depth at a delivery interface of typically 0.25 mm or 0.50 mm for a radioactive fluid such as xenon 133 gas. A typical radiation dose rate for a balloon catheter of the present invention can typically be in the range of 2 to 10 cGy per minute per millicurie (mCi).

The radiation dose rate of a balloon material is a function of or is dependent upon the thickness of the balloon material, the density of the balloon material, and/or the volume of the balloon. In addition, the volume is, in turn, dependent upon the length of the radiation source and, in particular, the longitudinal length of the balloon along with the diameter and radius of the balloon. The axial length of the balloon is important with respect to the radiation source in that accumulative dosimetry effects (scatter, coincidence, photo electric) are achieved with the radioactive fluid disposed along the length of the catheter. The radiation dose rate is also affected by the surface area of the inflatable balloon in response to the radioactive fluid.

Radiation source activity is a function of the radioactive fluid or preferably of the radioactive gas that is used with the radiation treatment. As described hereinafter, radioactive xenon 133 gas is preferred in that it is an inert gas that provides synchronous gamma and beta radiation emission with a half life of approximately five days. Concentrations of xenon 133 gas can typically range from 10 mCi to 150 mCi per cc or more of gas volume at the time of calibration.

Radiation exposure time is prescribed by the attending physician, commonly with a speciality in radiation oncology, nuclear medicine or nuclear oncology. Exposure times range from less than a minute upwards to ten minutes, depending on the activity of the radiation source. Particular concentrations of the radiation source are normally provided with commercially available radiation sources. These concentrations are used by the physician to determine radiation exposure time. The radiation dose rate is a function of the properties of delivery devices such as catheter apparatus 20, which in turn is a function of balloon material thickness, density and volume as previously indicated. External or internal brachytherapy medical radiation delivery apparatus can be experimentally dose calibrated and verified by a radiation physician specialist, medical physicist, or certified radio/nuclear laboratory, or with approved device-specific computer software for patient treatment. With such a calibrated radiation dose rate, the physician can calculate and prescribe the required radiation source concentrations and exposure times for treatment of the patient. The calibration of the delivery device typically includes positioning the delivery apparatus in a phantom and positioning radiation detectors/sensors at a prescribed distance away from the delivery apparatus in the phantom. A series of measurements are used to graph the radiation from a series of radioactive fluid concentrations applied thereto. Such calibration is necessary and demanded by various regulatory agencies so that the radiation treatment provided to a patient is within specified limits of the prescribed total radiation dose. In addition, multiple radiation safety profiles are evaluated for handling and delivery.

Figure 26:
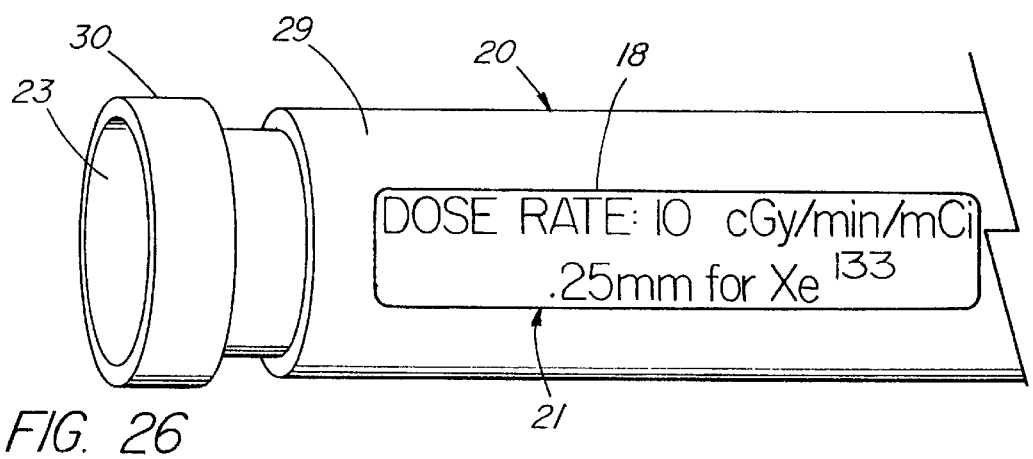
FIG. 26 is an enlarged, pictorial, proximal end view of the catheter apparatus of FIG. 1 with a radiation dose rate indicated thereon.

FIG. 26 depicts an enlarged, pictorial, proximal end view of catheter apparatus 20 of FIG. 1. In this particular embodiment, the radiation dosimetry unit of measurement 18 is the radiation dose rate, which is indicated as 10 cGy/min/mCi at a tissue depth of 0.25 mm for a radiation source of xenon 133. With this radiation dosimetry unit of measurement indicated on the catheter, an attending physician can readily calculate and prescribe a desired total radiation dose for a patient with commercially available radiation concentrations of, for example, Xenon 133 and a calculated radiation exposure time as a verified standard for a particular catheter/balloon make, style, and size. As a result, the attending physician eliminates the need to perform more laborious calculations and independent measurements, or having the delivery device sent to a medical physicist or laboratory for calibration of the radiation dose rate of the delivery device.

In addition, the catheter is made in a uniform-single construct with a gas-tight injection port component, which is leak-proof and injection "friendly" and has a septum of "resistant" synthetic rubber (Viton), which minimizes risk of leak or xenon adsorption. Furthermore, a leak-tight directional valve controls and locks direction of radiofluid passage for safety. A standard-type catheter would not provide this.

Although the indicator is affixed, positioned, disposed, connected to, on, or about the proximal end of the catheter for visualization by the attending physician, this indicator 21 is normally indicative of the portion of the delivery system such as the inflated balloon of a balloon catheter, which is inflated for the purposes of making contact with tissue to be treated.

More particularly, the indicator and the radiation dose rate is indicative of the material that comes in contact with the tissue to be treated. By way of example, the outer surface or wall of the balloon catheter along with the density and thickness thereof are one of the major factors in determining the radiation dose rate. This radiation dosimetry unit of measurement is experimentally calculated or computer modeled and verified with experimental calculations and applied preferably to the proximal end of the delivery system. The indicator of the dosimetry unit can be printed or painted on the outer surface of the catheter, embossed in or raised from the outer surface of the delivery system. The indicator can comprise at least one of a plurality of symbols, letters or numbers disposed on the radioactive delivery system for indicating the dosimetry unit of measurement. It is also contemplated that any indicator of whatever type can be affixed, disposed or positioned on the delivery system for the purposes of indicating at least one radiation dosimetry unit of measurement. Not only can the radiation dosimetry unit of measurement be directed to the portion of the delivery system that comes in contact with the tissue to be treated, but also radiation indicators such as incidental radiation dose rate, which is important to attending personnel to minimize their exposure to radiation.

Figure 27:
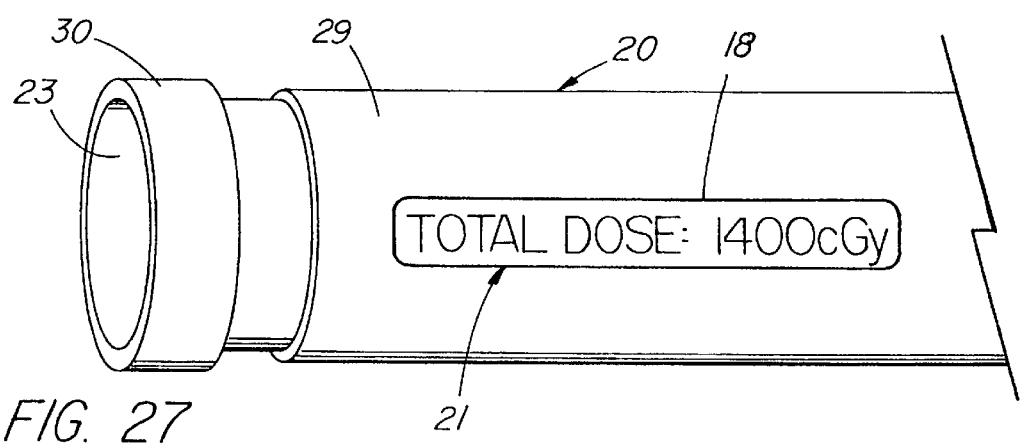
FIG. 27 is an enlarged, pictorial, proximal end view of the catheter apparatus of FIG. 1 with a total radiation dose indicated thereon.

FIG. 27 depicts an enlarged, pictorial, proximal end view of catheter apparatus 20 of FIG. 1 in which the radiation dosimetry unit of measurement 18 is indicated as total dose and, in particular, a total radiation dose of, for example, 1400 cGy. This indicator 21 is thus printed, embossed, or raised and indicated as total dose. Inflation lumen 23 extends longitudinally through elongated member 29 of catheter apparatus 20. A gas tight fitting/hub 30 is affixed in a well-known manner to elongated member 30 of catheter apparatus 20. These particular components of catheter apparatus 20 are also depicted in FIGS. 25 and 26. Elongated member 29 comprises a polyurethane, polyethylene, polyimide, polyvinyl chloride, polyamide, polytetrafluoroethylene, silicone, or any other suitable material. The selection of the catheter material is typically dependent on the particular anatomical site that the catheter apparatus is to be positioned or extended through. These elongated member materials can also be coated with a hydroph slip coating to further ease insertion and introduction to the treatment site. In addition to well-known hydrophillic slip coatings, the inner and/or outer surfaces of the elongated member can be treated such as with ion beam bombardment or deposition, which is commercially available from the Spire Corporation, Bedford, Mass. Ion beam bombardment or deposition can significantly alter the surface energy density of the elongated member material to reduce adhesion of thrombus or other agents thereon. This treatment is also known to provide an antibacterial, antifungal, or an antithrombogenic surface.

As indicated, determining the dosimetry for a catheter of given structural parameters and known quantity of source radiation, makes it possible for a physician to select a pre-labeled, referenced catheter having the desired treatment parameters. To further aid the physician in selection of the proper catheter, this displayed nominal dosimetry for a specific type of radiation delivery catheter could represent the expected dose in mCi of xe-133 that the average patient would receive at a set distance from an injected balloon source for a specific balloon size and standard injected dose. Alternate designations can include average total body exposure or bedside dose for a patient per treatment for a given dose and/or treatment time, and/or the expected average exposure to bedside personnel, including expected dose at a given distance from the injected balloon source, and total superficial dose per treatment for a given dose and/or treatment time.

Identification of the expected average dose for a given distance from the delivery source, or on a total exposure per treatment basis, can simplify the process of deciding on a treatment plan. Catheters can be made available in a range of diameters and balloon sizes to accommodate the anatomical requirements of different treatment sites. For example, the text accompanying the identification for a 3.5 mm×40 mm balloon catheter might include, "This catheter will provide, on average, a bedside dose exposure of $\leq 5$ mR/hr (for a standard reference of 300 mCi injected, balloon within patient, for average treatment time of $\leq 2$ min, at the site of injection"). Additional text might include, "This catheter system will provide $\leq 2.5$ mR per use to bedside personnel, according to standard of reference (reference as total external dose from any average leak plus point source as to above parameters"). Minimized or limited specific range of routine radiation exposure to the patient from the delivery system before, during, and after the required dose delivery should be limited to a total body dose and/or whole organ dose ranging between $\leq 5$ rem and $\leq 50$ rem; more ideally between $\leq 1$ rem and $\leq 5$ rem; and most ideally between $\leq 50$ mrem and $\leq 100$ mrem. For healthcare personnel, the total body dose and/or whole organ dose limits should be between $\leq 1$ rem and $\leq 5$ rem, with a more ideal range of $\leq 100$ mrem to $\leq 500$ mrem, and a most ideal range of $\leq 1$ mrem to $\leq 5$ mrem.

To minimize radiation exposure to attending personnel elongated member 29 of catheter apparatus 20 can include a high density material to absorb and/or block the radiation from the radioactive fluid when in inflation lumen 23. By way of example, this high density material can constitute a loading of greater than 30 percent by weight of, for example, barium, tungsten, lead, tantalum, titanium, bismuth, gold, platinum, palladium or rhodium.

Referring the reader's attention to FIGS. 1–4 and 6–8, the portion of the delivery system such as balloon 22 through which radiation from a radioactive fluid is normally directed includes at least one of silicone, latex, a synthetic material similar to latex, polyamide, vinyl, polyethylene, polytetrafluoroethylene, polyethylene terephthalate, fluorinated ethylene propylene, or any other suitable material. The balloon material can also include a loading of high density material to absorb or block radiation and thereby consequentially redirect the radiation to the treatment site. This material can also block or lessen radiation exposure of blood passing through the balloon sections. This high density material can be a loading of greater than 20 percent by weight of at least one of barium, tungsten, lead, tantalum, titanium, bismuth, gold, platinum, palladium or rhodium. The radiation dose rate of the balloon can also be altered or redirected by applying a thin coating of a metal or other reflecting materials to the various inner and outer surfaces of the balloon as herein later described.

FIG. 28 depicts an enlarged, pictorial, proximal end view of catheter apparatus 20 of FIG. 1 with an alternative embodiment of indicator 21 affixed, disposed or positioned thereon. Indicator 21 includes a housing or holder 19 as depicted in which a radiation sensitive film 31 is positioned therein. The arrow indicates the placement of radiation sensitive film 31 into indicator holder 19. Positioned adjacent to aperture 33 on the indicator is a visible shades scale 35 having various shades of gray between white and black at the opposite ends thereof. When exposed to various dosages of radiation, radiation sensitive film 31, such as a Gafchromic type film from, for example, Nuclear Associates of Carle Place, N.Y., changes color. The Nuclear Associates' Gafchromic film exhibits various hues of blue in response to radiation. This change in color is visible as a change from clear to black with various shades of gray therebetween. The various shades of gray or blue indicate the amount of radiation that film 31 has been exposed to. Thus, the attending physician can readily match the visible shade of radiation sensitive film 31 with gray scale 35 to determine the radiation dose and activity of the radiation source. For purposes of convenience, total dose amounts can be printed or indicated right next to each shade of gray on gray scale 35.

FIG. 29 depicts an enlarged longitudinal sectioning of elongated member 29 of catheter apparatus 20 through indicator 21. Radiation sensitive film 31 is inserted into channel 37 of the indicator for visual reading of the change in color of the film. The bottom material 39 of indicator 21 is preferably selected to be that of the material coming in contact with the tissue to be treated. Even more preferably, the bottom material is selected to be of equal thickness along with the same loading of the high density material of the balloon material. This is to best approximate the radiation dose being applied through the balloon to the treatment site. Depending on the radiation volume size, the thickness and loading of the bottom material can be modified to more closely approximate the total radiation dosage being radiated at the treatment site.

FIG. 30 depicts an enlarged sectional view of an alternative embodiment of radiation sensitive film 31. In this embodiment, the radiation sensitive film is layered in a stair step configuration to provide a greater change in color or the gray scale depending on the type of radiation source being utilized.

FIG. 31 depicts still another alternative embodiment of radiation sensitive film 31 in which strips of radiation sensitive Gafchromic type film are butted end-to-end. Each strip or segment has a different sensitivity to radiation and thus can be utilized to indicate a much larger range of radiation doses being exposed thereto.

Figure 33:
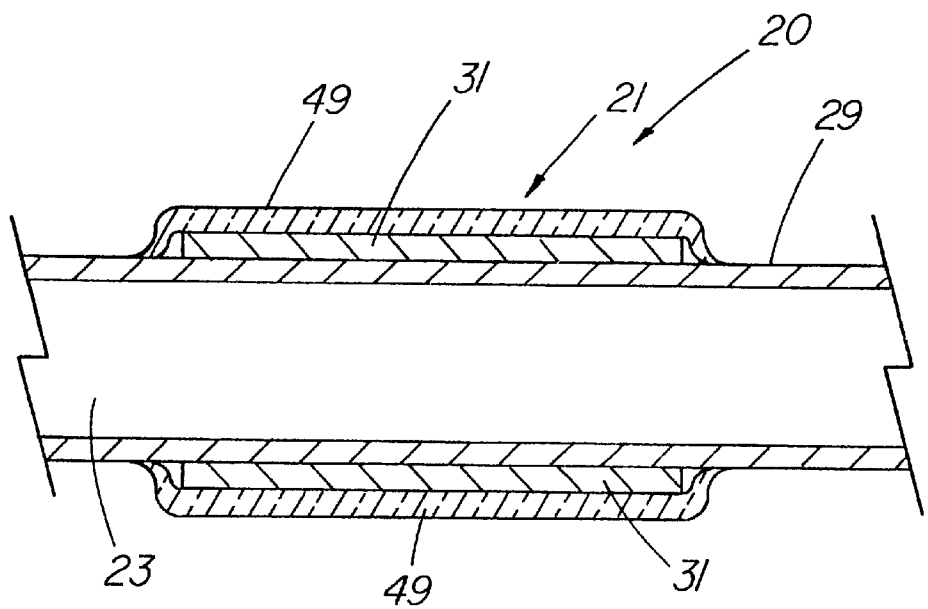
FIG. 33 is an enlarged, longitudinally sectioned, proximal end view of the catheter apparatus of FIG. 1 with still another alternative embodiment of an indicator thereon.

FIG. 33 depicts an enlarged, sectioned, proximal end view of catheter apparatus 20 of FIG. 1 with still another alternative embodiment of radiation indicator 21 thereon. In this particular embodiment, radiation indicator 21 includes radiation sensitive film 31 positioned around elongated member 29 of the catheter. The thickness of elongated member 29 underneath radiation sensitive film 31 is formed to approximate the relative thickness of the balloon catheter as well as the treatment depth of the tissue intended to be in contact with the balloon. As a result, the wall thickness of member 29 beneath radiation sensitive film 31 best approximates the balloon material and tissue so that the radiation sensed by film 31 is that at the desired tissue treatment depth. The xenon-133 radioactive gas resides in inflation lumen 23 of the elongated member as well as the inflatable balloon. Positioned over and around radiation sensitive film 31 is transparent material 49 such as clear silicone so as to hold the radiation sensitive film in position around the proximal end of the catheter apparatus. The clear transparent property of this material or other similar materials provides for minimal distortion of the hue or color of the radiation sensitive film.

Figure 34:
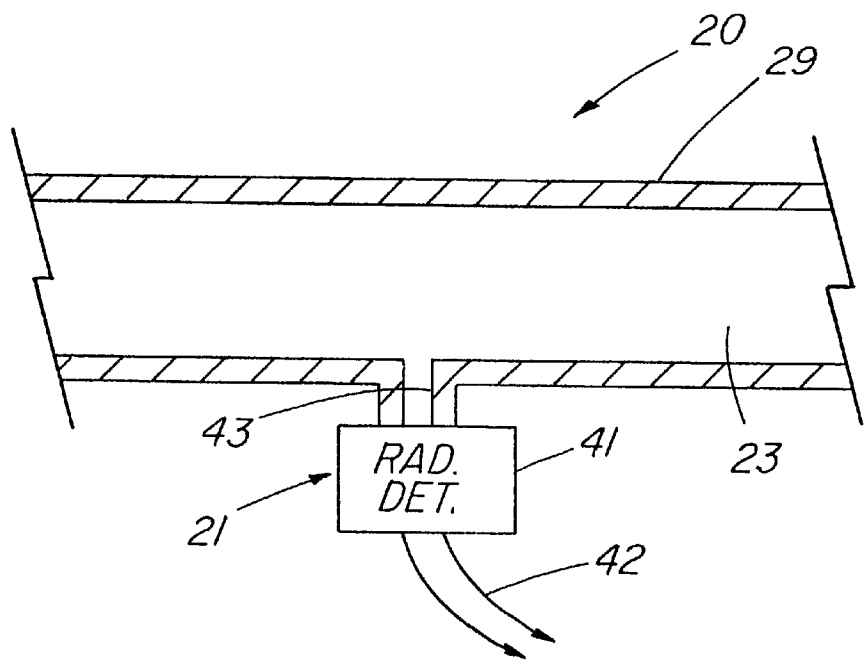
FIG. 34 is an enlarged, longitudinally sectioned, proximal end view of the catheter apparatus of FIG. 1 with yet still another alternative embodiment of an indicator thereon.

FIG. 34 depicts an enlarged, sectioned, proximal end view of the catheter apparatus 20 of FIG. 1 with yet still another embodiment of indicator 21 disposed thereon. In this particular embodiment, the radioactive fluid not only passes through inflation lumen 23 of elongated member 29 but also out of side port 43 to electronic radiation detector 41. This electronic radiation detector is commercially available and is an electronic ion exchange detector. Electrical conductor leads 42 extending from the radiation detector are connected to an electronic display unit such as an LCD or LED display for displaying radiation level(s).

Figure 32:
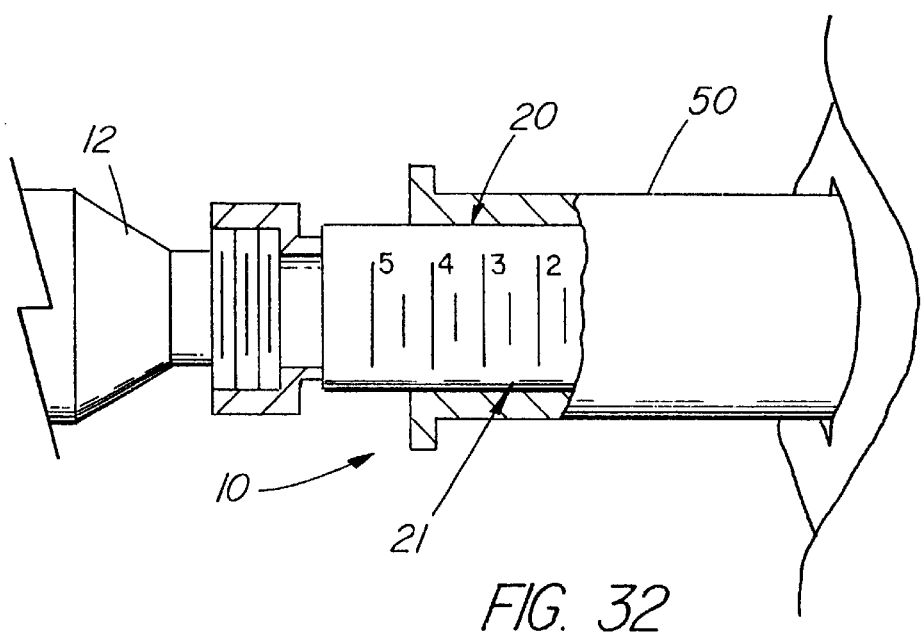
FIG. 32 is an enlarged, partially sectioned view of the catheter apparatus of FIG. 1 with a dosimetry unit indicator thereon.

Returning the reader's attention to FIGS. 1–6, the method of the present invention is designed to apply ionizing radiation prophylactically to post-angioplasty vascular tissue or tumors disposed internally within a patient while minimizing exposure of healthy tissue. Initially, the location and the size of the lesion 40 to be treated are clinically identified, perhaps, with a fluoroscope. The catheter apparatus 20 is then introduced and positioned adjacent to the lesion 40. The plurality of discrete balloon sections 22, 24, and 26 of a special, hypo-dense, thin material enable the inflated catheter apparatus 20 to more closely match and/or conform with the internal tissue wall, and minimize the amount of internal gas loss in the event of leakage. The catheter apparatus 20 includes an outer retractable radiation sleeve or shield 50 to prevent the exposure of healthy tissue adjacent to the lesion to radiation. After the catheter apparatus 20 is positioned alongside the lesion 40, the radiation shield 50 is retracted to a specific measurable length as depicted in FIG. 32. This specific length controls dosage rate and radiation source volume size. The balloon sections 22, 24, and 26 are then inflated with the radioactive fluid exposing the lesion 40 to the radiation dosage. The preferred gas, xenon or xenon isotope, emits beta and gamma particles into the lesion 40. Furthermore, indicator 21 can be used to establish dosage rate and total radiation dose.

The catheter apparatus 20 enables substantial blood or other fluid flow between the balloon sections 22, 24, and 26 when fully inflated. The balloon sections 22, 24, and 26 include a unique inner and outer surface 25 and 27 configuration. The radiation flow is directed through the outer surface 27 of the catheter apparatus 20 to the lesion 40 while exposure to radiation of the blood flowing internal to the catheter apparatus 20 is minimized. Accordingly, the inner surface 25 is more attenuating to the transmission of radiation than the outer surface 27. Either the inner surface (wall) 25 is thicker than the outer surface (wall) 27 as shown in FIG. 7, or the inner surface 25 includes a layer of material that is resistant to the penetration of radiation (not shown).

When a multiple balloon system is used, preferably either three discrete balloon sections are used as shown in FIGS. 1 through 6, or four balloon sections 22, 24, 26, and 28 with interposed sections 32, 34, 36, and 38 can be used as shown in FIGS. 9 and 10.

One primary application of the system of the present invention is for use after standard, angioplasty procedure: including multiple lesions at one treatment session. Controlled internal radiation therapy is provided to an artery or vessel for the prevention of arterial restenosis due to smooth muscle hyperplasia or similar related pathology. This will enable cannulation via the same access port from the pre-emptive dilatation procedure.

Discrete balloon sections or segmented systems 22, 24, and 26 or possible variants thereof are specifically structured to enable the application of a radioactive gas for therapeutic intent.

FIGS. 11 through 16 disclose another embodiment of catheter apparatus 120 of the present radiation delivery device invention. Drafted segmental and peripheral "tire-like" balloon sections or segment configurations 115 optimize direct circumferential abutment of the entire lumen wall. This will minimize intraluminal attenuation factors and maximize homogeneous dose rate delivery, conforming and enabling irregularly-shaped intimal surfaces. Also, when the catheter segments 115 are pressurized and expanded, a significant residual rate of intraluminal blood flow is enabled internal to the segments.

The catheter apparatus of the present invention is designed to minimize the secondary risk of medical complications caused by blood flow deficiency due to underlying disease or vasospasm in the peripheral, kidney, and, particularly, the heart vessels. The centrally directed perfusion flow can also contribute to outwardly directed pressure gradients, therefore, further supporting and stabilizing the radioactive-gas expander balloons against the arterial wall.

The catheter apparatus of the present invention enables individual patient flexibility as to dosage, treatment exposure time, and lesion segment lengths. Also, since blood flow cannot be completely occluded during therapy, radiation time need not be limited to less than three minutes, and therefore, very high energy gamma emitters or radiation activity levels are not needed. More expensive loading devices, shielded treatment rooms, and solid radio sources are thereby avoided. Also, healthy tissue is not unnecessarily exposed to passing or placement-preparation time irradiation as with other solid-source systems.

If inadequate blood flow rates or distal symptoms occur, this closed, sealed and inert radioactive gas system 10, 110 can be easily deflated without exposing the patient or medical personnel to real radiation risk. After flexibly allowing for several minutes of reperfusion time, the catheter apparatus 20, 120 can be simply reinflated and the prescribed treatment time/dose (several times if needed) is resumed without diminishing the therapeutic benefit.

Furthermore, the system of the present invention enables the treating therapeutic radiologist to address more than one vessel system or lesion even distal to the distribution of the primary lesion that may require subjective variation in post-dilatation balloon length and diameter due to sensitivity of distal ischemic-prone tissue from risk of prolonged diminished blood flow.

The sectioned, segmented or compartmentalized radioactive gas delivery tracks communicating with the end point expander balloons, will minimize the potential volume of gas leak should a balloon lose integrity. The residual catheter gas volume may be withdrawn into the shielded syringe without further leakage. The bloodstream released gas poses no real radiation or chemical threat to the patient, because of the physical and biological properties of the inert gas.

Figure 16:
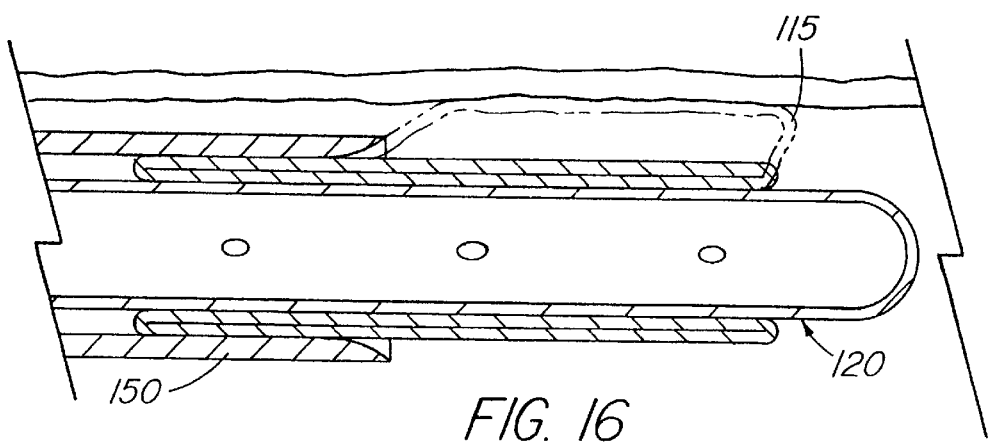
FIG. 16 is a detailed sectional view of the partially-inflated catheter apparatus of FIG. 11, complete with the retractable sleeve.

The length of the distal expandable component of the catheter apparatus 20 or 120 is covered by a thin, retroslidable or static sleeve 50 or 150, as shown in FIGS. 4 and 16, which is radiopaque for purposes of imaging localization. The sleeve 50 or 150 is in direct continuity with and manipulatable externally by the physician. The sleeve is positioned proximal to the access port to the balloon sections or segments. After confirmation of placement of the distal catheter apparatus 20 or 120 by fluoroscopic means, the catheter sleeve 50 or 150 is slowly pulled back, and a concordant ruler is exposed in parallel, measured in millimeters, whereby the treating physician accurately determines the length of the balloon to be expanded, and the length of the vessel wall to be treated 40 or 140. Alternatively and preferably, indicator 21 can be utilized to establish selectively the dosage rate as illustrated in FIG. 32. This will enable immediate confirmatory calculations as to specific dose rates, treatment time, and the volume of the radioactive gas injected.

The proposed radioactive gas or gases emit gamma photons enabling imaging and semi-log calculations to be performed at bedside using a conventional gamma camera and computer (not shown), which is left on the monitor distal to the treatment field to detect any early leakage for concerned physicians at minimal additional cost.

Although the lumen diameter is narrow and contains only a small fraction of the total volume of radioactive gas injected per session, the designed shielding properties of the sleeve 50 or 150 or outer lumen wall layer minimize any significant normal tissue or blood cell exposure over the remaining non-inflated catheter length, particularly with the energies of emission of the isotopes selected.

The interval and possibly staggered placement design of the entry portals and columns between the catheter body and expansion "modules" or balloons enable cutoff control of the balloon expansion length due to the controlled length of outer sleeve retraction.

The primary rationale and benefits for the therapeutic application of radioactive xenon gas with the "ASP" or similar catheters for intravascular brachytherapy, enable precise determination of total dose, dose rate, and depth distribution of radiation emitted from a source.

Radioactive xenon-133 gas, and less commonly used xenon-127 gas and krypton-85, as well as, technetium compounds, have been widely used for several years and proven relatively safe within medically accepted radiation levels for nuclear diagnostic studies involving the lung and the measurement of blood and fluid flow rates through vessels to specific organs. When used as an unsealed free-gas form, the inert, noble gas properties essentially enable the molecules to rapidly dissipate throughout the body of the patient or through a room, without any prolonged organ accumulation or interaction within specific dose ranges. Rapid expulsion of the relatively lower energy nuclear emissions of the xenon, is quickly re-released from the bloodstream through the lungs.

Xenon is a very stable element which can be pressurized, stored, and made to high millicurie activity per cubic centimeter (cc) with very reasonable cost and availability.

Xenon-133 provides both a beta particle (101 keV avg.; 364 keV max.), and at least two usable photons (32 keV 48 percent; 81 keV 37 percent).

The beta particles offer excellent initial dose rate delivery when directly adjacent to the tissue with the first millimeter. The particle does not penetrate much beyond the first millimeter of tissue, thereby not contributing to any significant distal normal tissue exposure.

The gamma photon energies and their decay fractions provide complementary dose deposition for the first millimeter, and primary dose delivery for an additional several millimeters of arterial wall and adjacent tissue. The high percent of attenuated, and lower energy photons beyond this point provide for ease of personnel protection with routine lead jackets, or by placing a cover over the external surface of the treated region. Furthermore, the sensitivity of a small field gamma camera provides simple image monitoring and dose evaluation simultaneously.

Xenon-133 is commercially available within a week in concentration ranges from 10 mCi to 150 mCi per cc or more of gas volume. Also, the cost is currently estimated to be less than a few hundred dollars a dose of 150 mCi. A single dose order can be used to treat several patients per day for a full week, as the physical half-life is 5.2 days. Also, no special equipment, storage, or delivery devices are necessary, except for routine facilities available in most nuclear medicine or radiation oncology departments.

In vivo and in vitro facilities with standard exhaust hoods or negative pressure rooms provide adequate protection for this sealed use of xenon gas. A metered dose can safely and readily be transported to nearly any treatment site by one person, and administered by one person without special radiation protection needs, such as is necessary with higher energy photon sources for conventional brachytherapy. The most expensive addition to a standard treatment room is a simple negative pressure ventilation system, as a backup safety mechanism.

Figure 17:
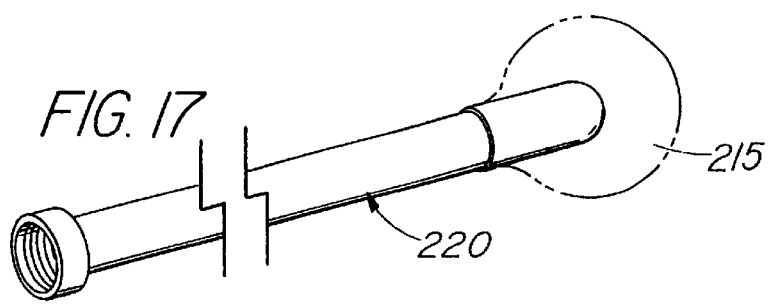
FIG. 17 is an isometric view of a fifth embodiment of the present invention disclosing a deflated catheter apparatus for use in treating malignancies in an organ such as the brain, esophagus, lung, or colon.
Figure 18:
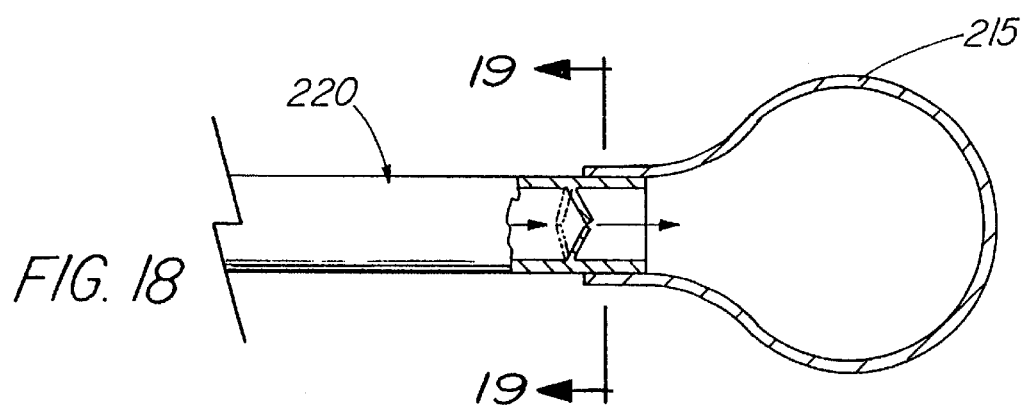
FIG. 18 is a detail view of the inflated catheter apparatus of FIG. 17.
Figure 19:
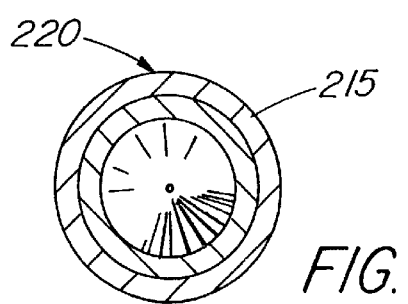
FIG. 19 is a detail sectional view of the pressure-sensitive flapper valve for the inflated catheter apparatus taken along line 19—19 of FIG. 18.

Selective balloon shapes and designs with various thicknesses and pliable lucent and radio penetrable materials enable site specific, intracavity or intraparenchymal insertion and localization from external origin and placement. FIGS. 17, 18, and 19 illustrate various other applications for catheter apparatus 220 which can include brain, lung, esophagus, trachea, cervix, biliary ductal system, colon or rectum, the gastrointestinal system, the gynecological system, and head and neck. All can optimize the self-introduction of radioactive xenon-133 or others, with controlled expansion and dose rate delivery while enabling individual tissue compliance such that the entire tissue is immediately and homogeneously adjacent to this high or low dose rate source without requiring surgical implant disruption, patient isolation, use of high energy concentrations of other radionuclides, patient or medical personnel risk from leakage, expensive materials, or costly radio-safe suite facilities.

The compliance, stress, and thickness properties of the balloons enable adequate and complete volume expansion against the variable surface of the arterial wall at less pressure than conventional therapeutic dilation plasty catheters.

Figure 20:
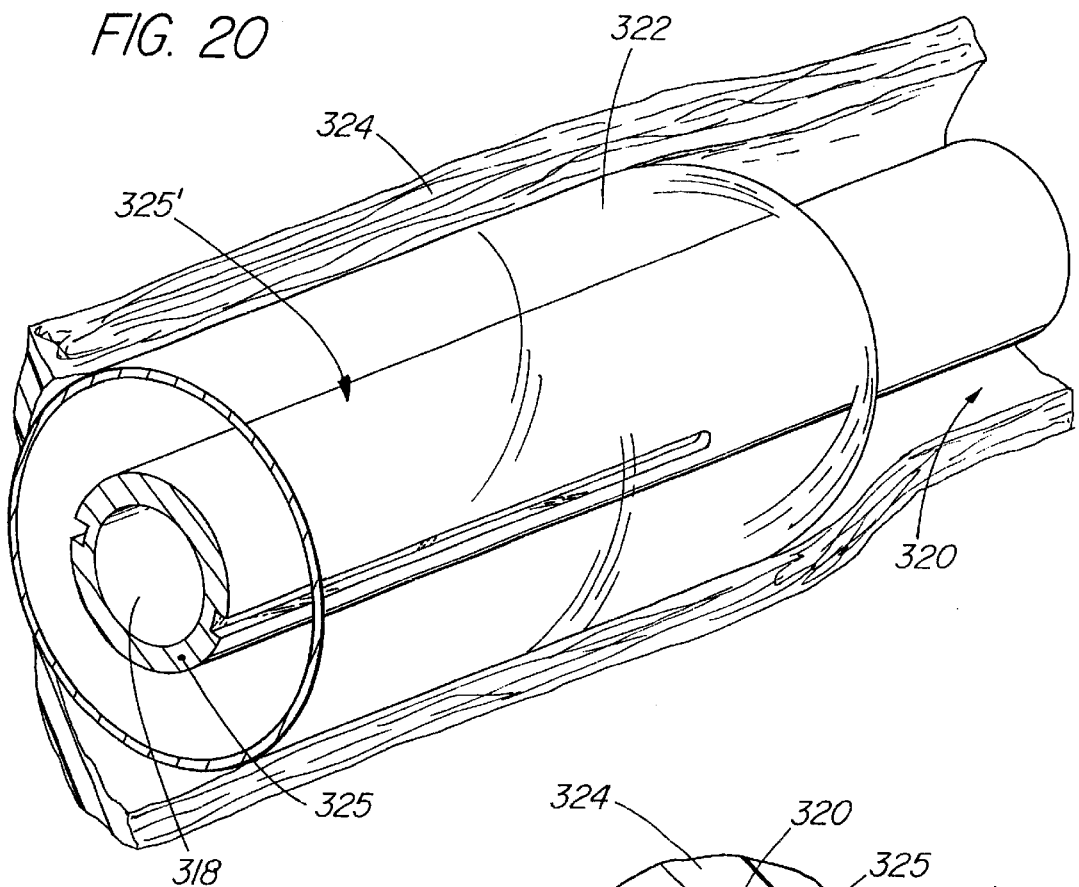
FIG. 20 is an enlarged assembly drawing of a sixth embodiment of the catheter system of the present invention, with a single balloon fully inflated as the blood flows through the center section of the apparatus.
Figure 21:
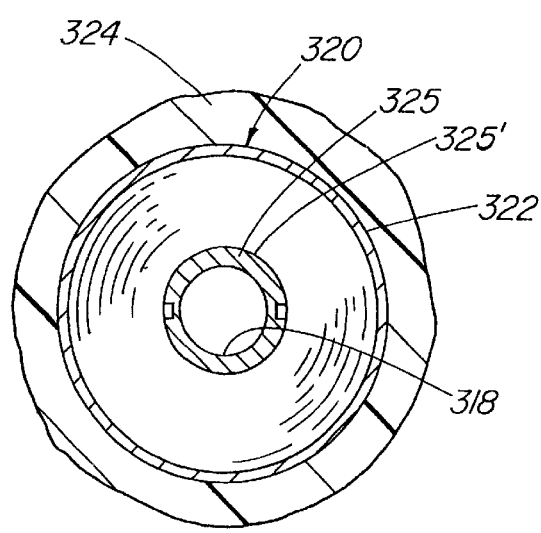
FIG. 21 is an end view of the catheter system of FIG. 20.

FIGS. 20 and 21 disclose yet another embodiment of the catheter apparatus 320, the catheter comprising an inner lumen 318 (with wall 325) for the transmission of blood when the catheter is inserted into a blood vessel. A specific coating of integrated and layered transitional metal or metal alloy compounds from the surface to the center of the exterior side 325' of the wall of the catheter lumen 318 protects the blood in the lumen from radiation, and enhances the radiation dosage delivered to the target. Either the heavy transitional metals or denser ranges of heavy metals are recommended, such as titanium, tungsten, aluminum, and germanium. The alloys can also include silicon. As used herein, the term "metal" includes pure metals, metal alloys, and metal alloy compounds.

FIG. 20 shows a balloon 322 extending around the inner lumen, and expanded by radiation fluid, the expanded balloon being in contact with the internal wall of a blood vessel 324. The lumen wall 325 attenuates the transmission dosage to the blood circulating through the hollow inner lumen of the central catheter apparatus 320. In addition, the system creates increased by-product radiation, bremsstrahlung and incidental scatter, from the impact of beta particles and gamma photons traveling into or toward the lumen wall 325. This energy, which would otherwise be wasted, produces by-product low-energy x-ray photons, which increase the deposited energy dosage into the target tissue via scattered angle coincidence or secondary redirected x-ray production from the slowing of beta particles traveling into or next to the metal compound on the wall surface 325'. These particles might ordinarily be considered too far from or having too little energy to reach the target tissue. However, the by-product x-rays (Bremmstrahlung radiation) travel through the balloon outer wall and deliver useful radiation dosage over a range of several hundred micrometers to the targeted tissue.

Figure 22:
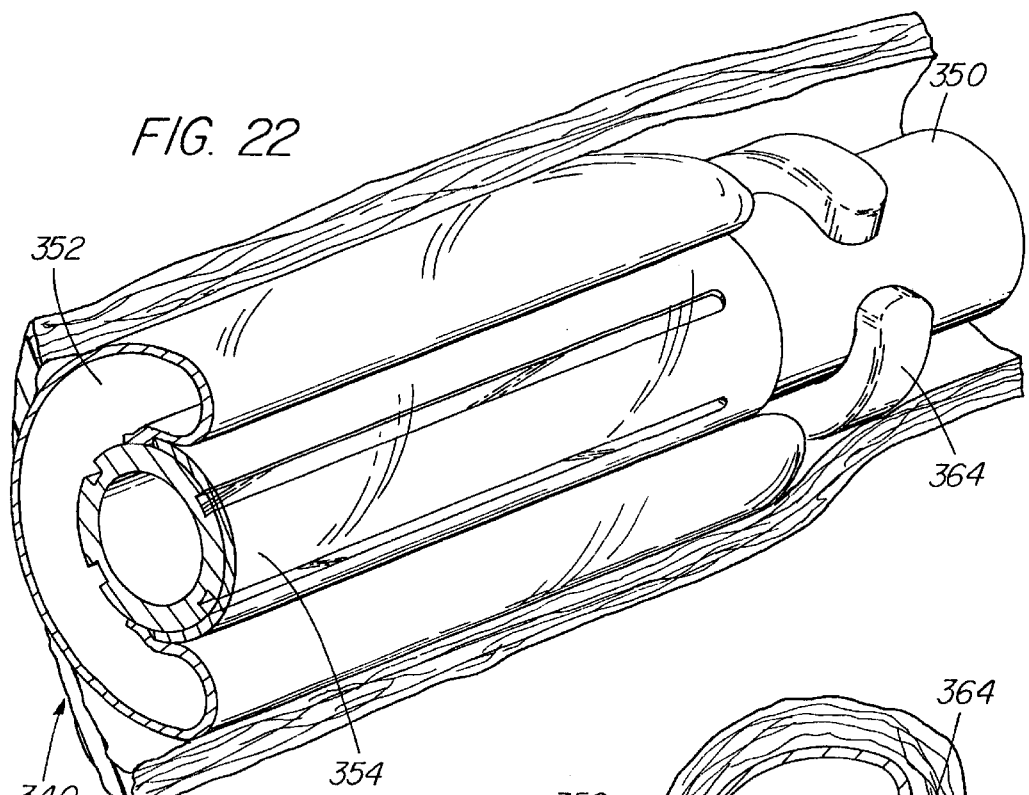
FIG. 22 is an enlarged assembly drawing of a seventh embodiment of the catheter system of the present invention, with two separate, semi-circular balloons, one balloon being inflated and delivering a treatment dose, while the opposing balloon is deflated.
Figure 23:
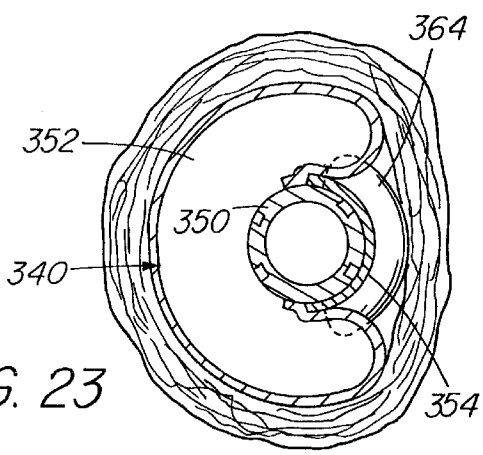
FIG. 23 is an isometric view of a end view of the catheter system of FIG. 22.
Figure 24:
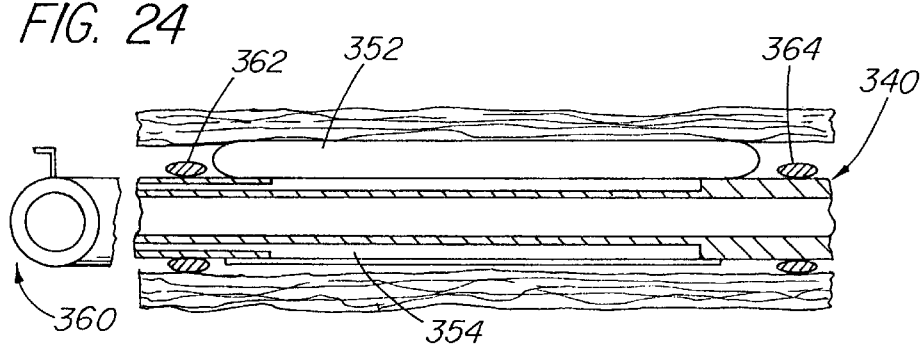
FIG. 24 is a side view of the catheter system of FIG. 22.

Still another catheter apparatus 340 is disclosed in FIGS. 22, 23 and 24. Two opposing and separate, semi-circular balloons 352 and 354 include opposed support displacers 362 and 364 attached just proximal and distal to the balloon lengths upon the outer lumen wall 350 of the inner lumen.

An injection port unit 360 enables fluid-tight redirection of radioactive fluid flow from between the balloons 352 and 354. Thereby, while one balloon 352 is inflated and delivering treatment dosage, the opposing balloon is deflated 354. The support displacers 362 and 364 are juxtaposed against the vessel wall enabling blood to flow more easily through the space opposite to the treatment side.

The single-unit injection port 360 with synthetic septum is fluid-tight and leak-proof. The port 360 is preferably made of Viton rubber, enabling easy needle penetration without loss of gas under pressure via leaky adaptive Luer lock additions.

The radioactive xenon gas can be partially dissolved in sterile saline or lipid-containing solution for solubilizing the xenon. The resulting material can then be injected into a balloon system.

It is also contemplated that the dosimetry unit of measurement indicator 21 disposed, affixed, or positioned on a delivery device can be an electronic display panel such as LCD or LED. The display panel indicator can be connected to an electronic radiation sensor or detector positioned at that portion of the device for treating tissue. Such displays and detectors are commercially available.

Figure 35:
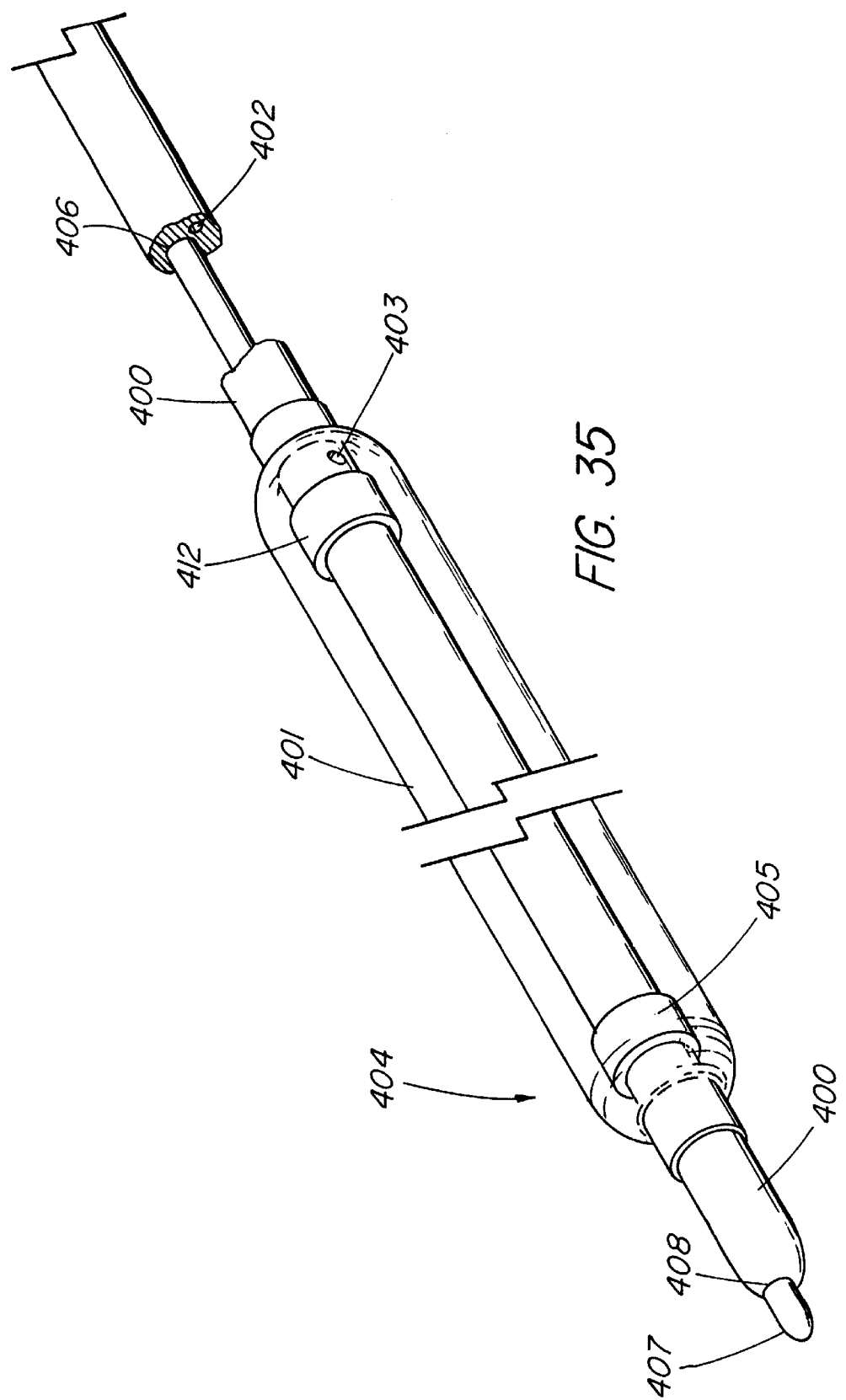
FIG. 35 is a partial perspective, partial sectioned view of yet another embodiment of the present invention.

Still another embodiment of catheter apparatus 400 is depicted in FIG. 35. A single angioplasty-style balloon 401 is mounted about the distal end 404 of the catheter 400. The balloon, which typically is under slight negative pressure just prior to treatment, is inflated with radioactive fluid that travels though inflation lumen 402 and enters the balloon at inflation port 403. In this embodiment, the inflation lumen 402 is made much smaller than in a typical balloon catheter 400 in order to minimize the amount of radioactive fluid in the catheter during treatment. This has the advantage of reducing potential exposure to the operator and non-target tissue of the patient, as well as reducing the amount of the costly radioactive source material needed to achieve the desired dosimetry at the treatment site. The size of the inflation lumen 402 is primarily limited by the tooling required to form the small lumen, typically, but not limited to approximately 0.010" in diameter. Radiopaque markers 405, 412 positioned near the proximal and distal ends of the balloon 401 aid the operator in placement of the balloon 401 under fluoroscopy. An alloy of tungsten and iridium makes an excellent radiopaque material, but almost any biocompatible radiopaque material can be used. The catheter 400 further includes a second lumen 406 through which a wireguide 407 can be introduced to assist in placement of the balloon 401 at the treatment site. The wireguide lumen is sufficiently large (typically over 0.020" in.) to accommodate a standard coronary wireguide. The wireguide 407 exits the catheter 400 through an orifice 408 at the catheter's distal end 404.

Figure 41:
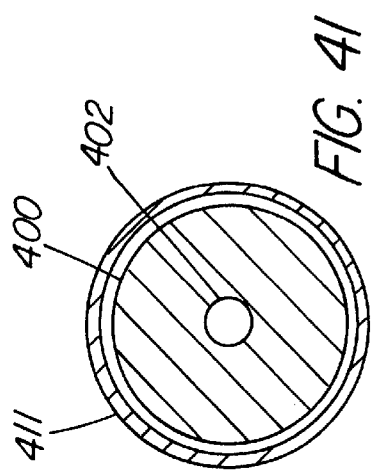
FIGS. 36–41 are cross sectional views of alternative embodiments of the present invention.
Figure 38:
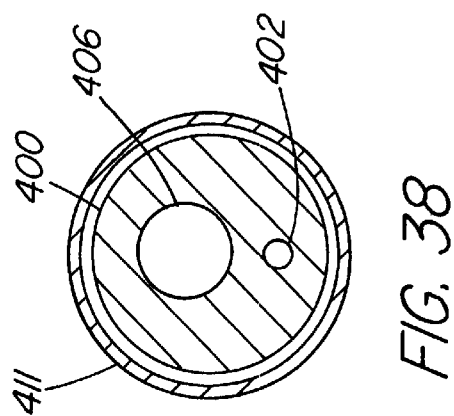
Figure 40:
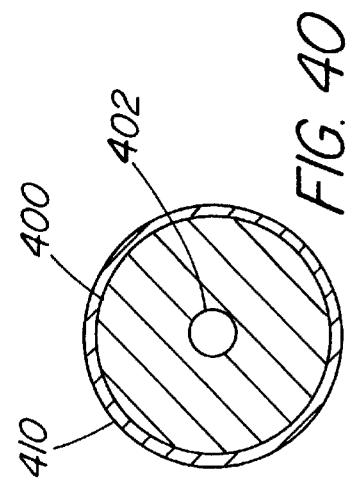
Figure 37:
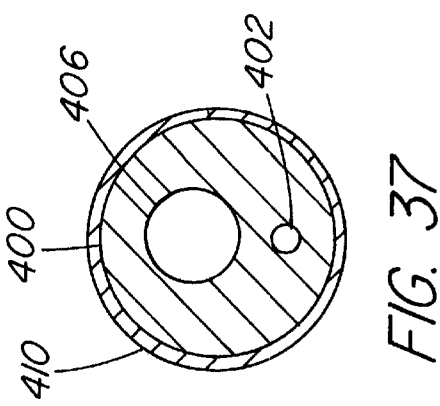
Figure 39:
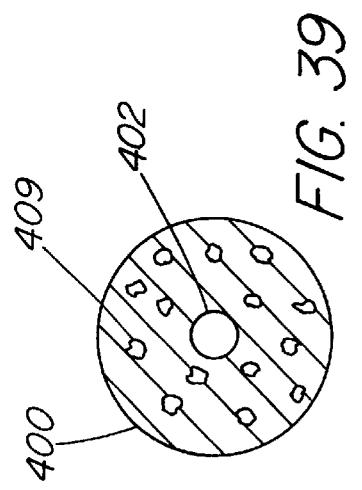
Figure 36:
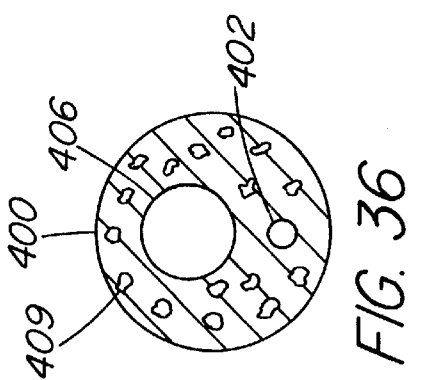

FIGS. 36–41 depict alternative methods of providing shielding to protect the patient and/or operator from radiation outside of the intended balloon source. FIGS. 36–38 are cross-sectional views of the catheter embodiment of FIG. 35, while FIGS. 39–41 represent cross-sectional views of a catheter embodiment similar to FIG. 35, except lacking the second larger guidewire lumen 406. FIGS. 36 and 39 depict a catheter 400 that has been loaded with a high density shielding material 409 including, but not limited to barium, tungsten, lead, tantalum, titanium, bismuth, gold, platinum, palladium, rhodium, or any other similar suitable material, or a combination thereof. A load of 20% barium sulfate, provides good shielding properties and excellent radiopacity without comprising the integrity of the catheter. Much higher amounts of shielding material can cause failure of the bonds between the balloon material and the catheter. FIGS. 37 and 40 depict catheters 400 that have had shielding added by the addition of a layer 410 of metal ions that have been deposited on the outside surface of the catheter 400 by a technique such as ion beam deposition (Spire Corp., Bedford Mass.). Another method of producing such a layer would be to shrink or bond a plastic film containing metal ions to the outer surface of the catheter 400. FIGS. 38 and 41 depict catheters 400 that are shielded by a outer sleeve or guiding catheter 411 which is loaded with a shielding material such as barium sulfate. Since bonding is not applicable for a such a sleeve, the amount of metal added to the plastic can be higher than that for the balloon catheter 400. The shielding sleeve 411 can comprise the entire length of the catheter (leaving the balloon portion exposed), or can be used only on the portion of the catheter that is outside the body in order to protect the operator handling the delivery system.

What is claimed is:

1. A medical radiation treatment delivery device comprising:
   a radioactive fluid delivery device (20) having at least a portion through which radiation from a radioactive fluid (12) is to be radiated to provide medical treatment, said at least portion of said radioactive fluid device having a radiation dosimetry unit of measurement indicative of the radiation that is to be radiated through said at least portion; and
   an indicator (21) affixed to said radioactive fluid delivery device and indicative of said radiation dosimetry unit of measurement, and
   said indicator including information that designates the expected dose in mCi of xenon-133 that the average patient would receive from the device.

2. A medical radiation treatment delivery device comprising:
   a radioactive fluid delivery device (20) having at least a portion through which radiation from a radioactive fluid (12) is to be radiated to provide medical treatment, said at least portion of said radioactive fluid device having a radiation dosimetry unit of measurement indicative of the radiation that is to be radiated through said at least portion, an indicator (21) affixed to said radioactive fluid delivery device and indicative of said radiation dosimetry unit of measurement, and said indicator including information that designates the average total body exposure for a patient per treatment for a given dose and/or treatment time.

3. A medical radiation treatment delivery device comprising:

a radioactive fluid delivery device (20) having at least a portion through which radiation from a radioactive fluid (12) is to be radiated to provide medical treatment, said at least portion of said radioactive fluid device having a radiation dosimetry unit of measurement indicative of the radiation that is to be radiated through said at least portion;

an indicator (21) affixed to said radioactive fluid delivery device and indicative of said radiation dosimetry unit of measurement, and said indicator including information that designates the expected average exposure to bedside personnel.

4. The device of claim 3, wherein said information includes the expected dose at a given distance from the injected balloon source.

5. The device of claim 3, wherein said information includes the total superficial dose per treatment for a given dose and/or treatment time.

6. A medical radiation treatment delivery device comprising:

a radioactive fluid delivery device (20) having at least a portion through which radiation from a radioactive fluid (12) is to be radiated to provide medical treatment, said at least portion of said radioactive fluid device having a radiation dosimetry unit of measurement indicative of the radiation that is to be radiated through said at least portion;

an indicator (21) affixed to said radioactive fluid delivery device and indicative of said radiation dosimetry unit of measurement, and said indicator including information expresses a standard of reference regarding exposure.

7. A medical radiation treatment delivery device comprising:

a radioactive fluid delivery device (20) having at least a portion through which radiation from a radioactive fluid (12) is to be radiated to provide medical treatment, said at least portion of said radioactive fluid device having a radiation dosimetry unit of measurement indicative of the radiation that is to be radiated through said at least portion;

an indicator (21) affixed to said radioactive fluid delivery device and indicative of said radiation dosimetry unit of measurement, and total routine radiation exposure to the patient from the delivery device is between 50 mrem and 50 rem.

8. The device of claim 7, wherein the total routine radiation exposure to the patient is between 50 mrem and 100 mrem.

9. A medical radiation treatment delivery device comprising:

a radioactive fluid delivery device (20) having at least a portion through which radiation from a radioactive fluid (12) is to be radiated to provide medical treatment, said at least portion of said radioactive fluid device having a radiation dosimetry unit of measurement indicative of the radiation that is to be radiated through said at least portion;

an indicator (21) affixed to said radioactive fluid delivery device and indicative of said radiation dosimetry unit of measurement, and a total body dose limit and/or whole organ dose limit is between 1 mrem and 5 rem.

10. The device of claim 9, wherein the total body dose limit and/or whole organ dose limit is between 1 mrem and 5 mrem.

* * * * *